United States Patent
Alexander

(10) Patent No.: US 9,332,992 B2
(45) Date of Patent: *May 10, 2016

(54) METHOD FOR MAKING A LAMINAR VENTRICULAR PARTITIONING DEVICE

(71) Applicant: CardioKinetix, Inc., Menlo Park, CA (US)

(72) Inventor: Miles D. Alexander, Fremont, CA (US)

(73) Assignee: CardioKinetix, Inc., Menlo Park, CA (US)

( * ) Notice: Subject to any disclaimer, the term of this patent is extended or adjusted under 35 U.S.C. 154(b) by 339 days.

This patent is subject to a terminal disclaimer.

(21) Appl. No.: 13/827,927

(22) Filed: Mar. 14, 2013

(65) Prior Publication Data

US 2013/0270735 A1 Oct. 17, 2013

Related U.S. Application Data

(63) Continuation-in-part of application No. 12/893,832, filed on Sep. 29, 2010, now Pat. No. 9,078,660, which is a continuation-in-part of application No. 11/860,438, filed on Sep. 24, 2007, now Pat. No.

(Continued)

(51) Int. Cl.
*B29C 43/18* (2006.01)
*A61B 17/12* (2006.01)
(Continued)

(52) U.S. Cl.
CPC ..... *A61B 17/12122* (2013.01); *A61B 17/12022* (2013.01); *A61B 17/12172* (2013.01); *B29C 43/18* (2013.01); *B29C 65/12* (2013.01); *A61B 2017/00243* (2013.01);

(Continued)

(58) Field of Classification Search
None
See application file for complete search history.

(56) References Cited

U.S. PATENT DOCUMENTS 3,874,388 A 4/1975 King et al.
4,007,743 A 2/1977 Blake (Continued)

FOREIGN PATENT DOCUMENTS

EP 1474032 A2 11/2004
EP 2068768 A 6/2009

(Continued)

OTHER PUBLICATIONS

Khairkhahan, Alexander; U.S. Appl. No. 113/954,221 entitled "Retrievable Cardiac Devices," filed Jul. 30, 2013.

(Continued)

*Primary Examiner* — Edmund Lee
(74) *Attorney, Agent, or Firm* — Shay Glenn LLP

(57) ABSTRACT

Described herein are systems and methods for securing a polymeric sheet to rib components of a frame structure, wherein the rib components are jointed at a hub to form an expandable and collapsible implant. In general, the method may include the steps of decreasing a diameter of the frame structure; placing the frame structure into an assembly fixture, wherein the assembly fixture is configured to hold the frame structure in a loaded configuration with a decreased diameter; placing a polymeric sheet into the assembly fixture; and heating the assembly under pressure to fuse the sheet to the frame structure. In general, a fixture may include a first and second platen having a shaping portion and a rim portion positioned around the periphery of the platen, wherein the shaping portions are configured to hold the rib components of the frame structure in a loaded configuration with a decreased diameter.

8 Claims, 25 Drawing Sheets

Related U.S. Application Data 7,897,086, which is a continuation-in-part of application No. 10/913,608, filed on Aug. 5, 2004, now abandoned, said application No. 12/893,832 is a continuation-in-part of application No. 12/509,289, filed on Jul. 24, 2009, now Pat. No. 8,398,537, which is a continuation of application No. 11/151,164, filed on Jun. 10, 2005, now Pat. No. 7,582,051.

(60) Provisional application No. 61/246,920, filed on Sep. 29, 2009.

(51) Int. Cl.
*B29C 65/12* (2006.01)
*A61B 17/00* (2006.01)

(52) U.S. Cl.
CPC ............ *A61B 2017/00867* (2013.01); *A61B 2017/12054* (2013.01); *A61B 2017/12095* (2013.01)

(56) References Cited

U.S. PATENT DOCUMENTS

| | | |
|---|---|---|
| 4,425,908 A | 1/1984 | Simon |
| 4,453,545 A | 6/1984 | Inoue |
| 4,536,893 A | 8/1985 | Parravicini |
| 4,588,404 A | 5/1986 | Lapeyre |
| 4,619,246 A | 10/1986 | Molgaard-Nielsen et al. |
| 4,685,446 A | 8/1987 | Choy |
| 4,710,192 A | 12/1987 | Liotta et al. |
| 4,819,751 A | 4/1989 | Shimada et al. |
| 4,832,055 A | 5/1989 | Palestrant |
| 4,917,089 A | 4/1990 | Sideris |
| 4,983,165 A | 1/1991 | Loiterman |
| 5,104,399 A | 4/1992 | Lazarus |
| 5,192,301 A | 3/1993 | Kamiya et al. |
| 5,192,314 A | 3/1993 | Daskalakis |
| 5,258,000 A | 11/1993 | Gianturco |
| 5,375,612 A | 12/1994 | Cottenceau et al. |
| 5,385,156 A | 1/1995 | Oliva |
| 5,389,087 A | 2/1995 | Miraki |
| 5,425,744 A | 6/1995 | Fagan et al. |
| 5,433,727 A | 7/1995 | Sideris |
| 5,451,235 A | 9/1995 | Lock et al. |
| 5,496,277 A | 3/1996 | Termin et al. |
| 5,527,337 A | 6/1996 | Stack et al. |
| 5,527,338 A | 6/1996 | Purdy |
| 5,549,621 A | 8/1996 | Bessler et al. |
| 5,551,435 A | 9/1996 | Sramek |
| 5,578,069 A | 11/1996 | Miner, II |
| 5,634,936 A | 6/1997 | Linden et al. |
| 5,634,942 A | 6/1997 | Chevillon et al. |
| 5,647,870 A | 7/1997 | Kordis et al. |
| 5,702,343 A | 12/1997 | Alferness |
| 5,709,707 A | 1/1998 | Lock et al. |
| 5,758,664 A | 6/1998 | Campbell et al. |
| 5,791,231 A | 8/1998 | Cohn et al. |
| 5,797,849 A | 8/1998 | Vesely et al. |
| 5,797,960 A | 8/1998 | Stevens et al. |
| 5,800,457 A | 9/1998 | Gelbfish |
| 5,800,517 A | 9/1998 | Anderson et al. |
| 5,829,447 A | 11/1998 | Stevens et al. |
| 5,833,698 A | 11/1998 | Hinchliffe et al. |
| 5,836,968 A | 11/1998 | Simon et al. |
| 5,843,170 A | 12/1998 | Ahn |
| 5,860,951 A | 1/1999 | Eggers et al. |
| 5,861,003 A | 1/1999 | Latson et al. |
| 5,865,730 A | 2/1999 | Fox et al. |
| 5,865,791 A | 2/1999 | Whayne et al. |
| 5,871,017 A | 2/1999 | Mayer |
| 5,875,782 A | 3/1999 | Ferrari et al. |
| 5,876,325 A | 3/1999 | Mizuno et al. |
| 5,876,449 A | 3/1999 | Starck et al. |
| 5,879,366 A | 3/1999 | Shaw et al. |
| 5,882,340 A | 3/1999 | Yoon |
| 5,910,150 A | 6/1999 | Saadat |
| 5,916,145 A | 6/1999 | Chu et al. |
| 5,924,424 A | 7/1999 | Stevens et al. |
| 5,925,062 A | 7/1999 | Purdy |
| 5,925,076 A | 7/1999 | Inoue |
| 5,928,260 A | 7/1999 | Chin et al. |
| 5,961,440 A | 10/1999 | Schweich, Jr. et al. |
| 5,961,539 A | 10/1999 | Northrup, III et al. |
| 5,984,917 A | 11/1999 | Fleischman et al. |
| 6,024,096 A | 2/2000 | Buckberg |
| 6,024,756 A | 2/2000 | Huebsch et al. |
| 6,036,720 A | 3/2000 | Abrams et al. |
| 6,045,497 A | 4/2000 | Schweich, Jr. et al. |
| 6,059,715 A | 5/2000 | Schweich, Jr. et al. |
| 6,076,013 A | 6/2000 | Brennan et al. |
| 6,077,214 A | 6/2000 | Mortier et al. |
| 6,077,218 A | 6/2000 | Alferness |
| 6,093,199 A | 7/2000 | Brown et al. |
| 6,095,968 A | 8/2000 | Snyders |
| 6,096,347 A | 8/2000 | Geddes et al. |
| 6,099,832 A | 8/2000 | Mickle et al. |
| 6,102,887 A | 8/2000 | Altman |
| 6,125,852 A | 10/2000 | Stevens et al. |
| 6,132,438 A | 10/2000 | Fleischman et al. |
| 6,142,973 A | 11/2000 | Carleton et al. |
| 6,152,144 A | 11/2000 | Lesh et al. |
| 6,155,968 A | 12/2000 | Wilk |
| 6,156,027 A | 12/2000 | West |
| 6,161,543 A | 12/2000 | Cox et al. |
| 6,193,731 B1 | 2/2001 | Oppelt et al. |
| 6,221,092 B1 | 4/2001 | Koike et al. |
| 6,221,104 B1 | 4/2001 | Buckberg et al. |
| 6,230,714 B1 | 5/2001 | Alferness et al. |
| 6,231,561 B1 | 5/2001 | Frazier et al. |
| 6,258,021 B1 | 7/2001 | Wilk |
| 6,267,772 B1 | 7/2001 | Mulhauser et al. |
| 6,290,674 B1 | 9/2001 | Roue et al. |
| 6,296,656 B1 | 10/2001 | Bolduc et al. |
| 6,312,446 B1 | 11/2001 | Huebsch et al. |
| 6,328,727 B1 | 12/2001 | Frazier et al. |
| 6,334,864 B1 | 1/2002 | Amplatz et al. |
| 6,343,605 B1 | 2/2002 | Lafontaine |
| 6,348,068 B1 | 2/2002 | Campbell et al. |
| 6,355,052 B1 | 3/2002 | Neuss et al. |
| 6,360,749 B1 | 3/2002 | Jayaraman |
| 6,364,896 B1 | 4/2002 | Addis |
| 6,387,042 B1 | 5/2002 | Herrero |
| 6,406,420 B1 | 6/2002 | McCarthy et al. |
| 6,419,669 B1 | 7/2002 | Frazier et al. |
| 6,436,088 B2 | 8/2002 | Frazier et al. |
| 6,450,171 B1 | 9/2002 | Buckberg et al. |
| 6,482,146 B1 | 11/2002 | Alferness et al. |
| 6,482,228 B1 | 11/2002 | Norred |
| 6,506,204 B2 | 1/2003 | Mazzocchi |
| 6,508,756 B1 | 1/2003 | Kung et al. |
| 6,511,496 B1 | 1/2003 | Huter et al. |
| 6,537,198 B1 | 3/2003 | Vidlund et al. |
| 6,551,303 B1 | 4/2003 | Van Tassel et al. |
| 6,572,643 B1 | 6/2003 | Gharibadeh |
| 6,586,414 B2 | 7/2003 | Haque et al. |
| 6,592,608 B2 | 7/2003 | Fisher et al. |
| 6,613,013 B2 | 9/2003 | Haarala et al. |
| 6,622,730 B2 | 9/2003 | Ekvall et al. |
| 6,645,199 B1 | 11/2003 | Jenkins et al. |
| 6,652,555 B1 | 11/2003 | Van Tassel et al. |
| 6,681,773 B2 | 1/2004 | Murphy et al. |
| 6,685,627 B2 | 2/2004 | Jayaraman |
| 6,702,763 B2 | 3/2004 | Murphy et al. |
| 6,730,108 B2 | 5/2004 | Van Tassel et al. |
| 6,776,754 B1 | 8/2004 | Wilk |
| 6,852,076 B2 | 2/2005 | Nikolic et al. |
| 6,887,192 B1 | 5/2005 | Whayne et al. |
| 6,951,534 B2 | 10/2005 | Girard et al. |
| 6,959,711 B2 | 11/2005 | Murphy et al. |
| 6,994,093 B2 | 2/2006 | Murphy et al. |
| 7,144,363 B2 | 12/2006 | Pai et al. |
| 7,172,551 B2 | 2/2007 | Leasure |
| 7,175,660 B2 | 2/2007 | Cartledge et al. |

(56) References Cited

U.S. PATENT DOCUMENTS

| | | |
|---|---|---|
| 7,279,007 B2 | 10/2007 | Nikolic et al. |
| 7,303,526 B2 | 12/2007 | Sharkey et al. |
| 7,320,665 B2 | 1/2008 | Vijay |
| 7,399,271 B2 | 7/2008 | Khairkhahan et al. |
| 7,485,088 B2 | 2/2009 | Murphy et al. |
| 7,530,998 B1 | 5/2009 | Starkey |
| 7,569,062 B1 | 8/2009 | Kuehn et al. |
| 7,582,051 B2 | 9/2009 | Khairkhahan et al. |
| 7,674,222 B2 | 3/2010 | Nikolic et al. |
| 7,758,491 B2 | 7/2010 | Buckner et al. |
| 7,762,943 B2 | 7/2010 | Khairkhahan |
| 7,824,325 B2 | 11/2010 | Dubi |
| 7,862,500 B2 | 1/2011 | Khairkhahan et al. |
| 7,887,477 B2 | 2/2011 | Sharkey et al. |
| 7,897,086 B2 | 3/2011 | Khairkhahan et al. |
| 7,938,767 B2 | 5/2011 | Evans et al. |
| 7,976,455 B2 | 7/2011 | Khairkhahan |
| 7,993,258 B2 | 8/2011 | Feld et al. |
| 8,192,478 B2 | 6/2012 | Khairkhahan et al. |
| 8,246,671 B2 | 8/2012 | Khairkhahan et al. |
| 8,257,428 B2 | 9/2012 | Khairkhahan et al. |
| 8,377,114 B2 | 2/2013 | Khairkhahan et al. |
| 8,382,653 B2 | 2/2013 | Dubi et al. |
| 8,388,672 B2 | 3/2013 | Khairkhahan et al. |
| 8,398,537 B2 | 3/2013 | Khairkhahan et al. |
| 8,500,622 B2 | 8/2013 | Lipperman et al. |
| 2001/0014800 A1 | 8/2001 | Frazier et al. |
| 2002/0019580 A1 | 2/2002 | Lau et al. |
| 2002/0026092 A1 | 2/2002 | Buckberg et al. |
| 2002/0028981 A1 | 3/2002 | Lau et al. |
| 2002/0032481 A1 | 3/2002 | Gabbay |
| 2002/0055767 A1 | 5/2002 | Forde et al. |
| 2002/0055775 A1 | 5/2002 | Carpentier et al. |
| 2002/0111647 A1 | 8/2002 | Khairkhahan et al. |
| 2002/0133227 A1 | 9/2002 | Murphy et al. |
| 2002/0161392 A1 | 10/2002 | Dubrul |
| 2002/0161394 A1 | 10/2002 | Macoviak et al. |
| 2002/0169359 A1 | 11/2002 | McCarthy et al. |
| 2002/0169360 A1 | 11/2002 | Taylor et al. |
| 2002/0183604 A1 | 12/2002 | Gowda et al. |
| 2002/0188170 A1 | 12/2002 | Santamore et al. |
| 2003/0045896 A1 | 3/2003 | Murphy et al. |
| 2003/0078671 A1 | 4/2003 | Lesniak et al. |
| 2003/0109770 A1 | 6/2003 | Sharkey et al. |
| 2003/0120337 A1 | 6/2003 | Van Tassel et al. |
| 2003/0135230 A1 | 7/2003 | Massey et al. |
| 2003/0149333 A1 | 8/2003 | Alferness |
| 2003/0149422 A1 | 8/2003 | Muller |
| 2003/0181942 A1 | 9/2003 | Sutton et al. |
| 2003/0220667 A1 | 11/2003 | van der Burg et al. |
| 2004/0002626 A1 | 1/2004 | Feld et al. |
| 2004/0034366 A1 | 2/2004 | van der Burg et al. |
| 2004/0044361 A1 | 3/2004 | Frazier et al. |
| 2004/0054394 A1 | 3/2004 | Lee |
| 2004/0064014 A1 | 4/2004 | Melvin et al. |
| 2004/0122090 A1 | 6/2004 | Lipton |
| 2004/0127935 A1 | 7/2004 | VanTassel et al. |
| 2004/0133062 A1 | 7/2004 | Pai et al. |
| 2004/0136992 A1 | 7/2004 | Burton et al. |
| 2004/0172042 A1 | 9/2004 | Suon et al. |
| 2004/0186511 A1 | 9/2004 | Stephens et al. |
| 2004/0215230 A1 | 10/2004 | Frazier et al. |
| 2004/0243170 A1 | 12/2004 | Suresh et al. |
| 2004/0260331 A1 | 12/2004 | D'Aquanni et al. |
| 2004/0260346 A1 | 12/2004 | Overall et al. |
| 2004/0267086 A1 | 12/2004 | Anstadt et al. |
| 2004/0267378 A1 | 12/2004 | Gazi et al. |
| 2005/0007031 A1 | 1/2005 | Hyder |
| 2005/0015109 A1 | 1/2005 | Lichtenstein |
| 2005/0038470 A1 | 2/2005 | van der Burg et al. |
| 2005/0043708 A1 | 2/2005 | Gleeson et al. |
| 2005/0065548 A1 | 3/2005 | Marino et al. |
| 2005/0085826 A1 | 4/2005 | Nair et al. |
| 2005/0096498 A1 | 5/2005 | Houser et al. |
| 2005/0113811 A1 | 5/2005 | Houser et al. |
| 2005/0113861 A1 | 5/2005 | Corcoran et al. |
| 2005/0124849 A1 | 6/2005 | Barbut et al. |
| 2005/0137690 A1 | 6/2005 | Salahieh et al. |
| 2005/0142180 A1 | 6/2005 | Bisgaier et al. |
| 2005/0177180 A1 | 8/2005 | Kaganov et al. |
| 2005/0187620 A1 | 8/2005 | Pai et al. |
| 2005/0216052 A1 | 9/2005 | Mazzocchi et al. |
| 2005/0228434 A1 | 10/2005 | Amplatz et al. |
| 2005/0277981 A1 | 12/2005 | Maahs et al. |
| 2005/0277983 A1 | 12/2005 | Saadat et al. |
| 2005/0283218 A1 | 12/2005 | Williams |
| 2006/0019888 A1 | 1/2006 | Zhou |
| 2006/0025800 A1 | 2/2006 | Suresh |
| 2006/0030881 A1 | 2/2006 | Sharkey et al. |
| 2006/0063970 A1 | 3/2006 | Raman et al. |
| 2006/0069430 A9 | 3/2006 | Rahdert et al. |
| 2006/0079736 A1 | 4/2006 | Chin et al. |
| 2006/0116692 A1 | 6/2006 | Ward |
| 2006/0136043 A1 | 6/2006 | Cully et al. |
| 2006/0199995 A1 | 9/2006 | Vijay |
| 2006/0229491 A1 | 10/2006 | Sharkey et al. |
| 2006/0259124 A1 | 11/2006 | Matsuoka et al. |
| 2006/0276684 A1 | 12/2006 | Speziali |
| 2007/0129753 A1 | 6/2007 | Quinn et al. |
| 2007/0135889 A1 | 6/2007 | Moore et al. |
| 2007/0162048 A1 | 7/2007 | Quinn et al. |
| 2007/0213578 A1 | 9/2007 | Khairkhahan et al. |
| 2007/0213815 A1 | 9/2007 | Khairkhahan et al. |
| 2008/0015717 A1 | 1/2008 | Griffin et al. |
| 2008/0045778 A1 | 2/2008 | Lichtenstein et al. |
| 2008/0228205 A1 | 9/2008 | Khairkhahan et al. |
| 2008/0319254 A1 | 12/2008 | Nikolic et al. |
| 2009/0054723 A1 | 2/2009 | Khairkhahan et al. |
| 2010/0030256 A1 | 2/2010 | Dubrul et al. |
| 2010/0057185 A1 | 3/2010 | Melsheimer et al. |
| 2010/0121132 A1 | 5/2010 | Nikolic et al. |
| 2010/0274227 A1 | 10/2010 | Khairkhahan et al. |
| 2011/0087066 A1 | 4/2011 | Boutillette et al. |
| 2011/0092761 A1 | 4/2011 | Almog et al. |
| 2011/0098525 A1 | 4/2011 | Kermode et al. |
| 2011/0178362 A1 | 7/2011 | Evans et al. |
| 2011/0264204 A1 | 10/2011 | Khairkhahan |
| 2012/0041257 A1 | 2/2012 | Stankus et al. |
| 2012/0245604 A1 | 9/2012 | Tegzes |
| 2012/0259356 A1 | 10/2012 | Khairkhahan |
| 2013/0090677 A1 | 4/2013 | Evans et al. |
| 2013/0165735 A1 | 6/2013 | Khairkhahan et al. |
| 2014/0296624 A1 | 10/2014 | Kermode et al. |
| 2014/0343356 A1 | 11/2014 | Nikolic et al. |
| 2015/0182338 A1 | 1/2015 | Kermode et al. |

FOREIGN PATENT DOCUMENTS

| | | |
|---|---|---|
| EP | 2344070 A | 7/2011 |
| EP | 2244661 B1 | 3/2012 |
| EP | 2082690 B1 | 6/2012 |
| JP | H08257031 A | 10/1996 |
| JP | 2001520910 A | 11/2001 |
| JP | 2003512128 A | 4/2003 |
| JP | 2003512129 A | 4/2003 |
| JP | 2005324019 | 11/2005 |
| JP | 2008508955 | 3/2008 |
| WO | WO 96/37859 A1 | 11/1996 |
| WO | WO 98/03213 A1 | 1/1998 |
| WO | WO 00/27292 | 5/2000 |
| WO | WO 00/42919 A1 | 7/2000 |
| WO | WO 00/50639 A2 | 8/2000 |
| WO | WO 01/30266 | 5/2001 |
| WO | WO 01/78625 | 10/2001 |
| WO | WO 02/30335 | 4/2002 |
| WO | WO 02/45710 A1 | 6/2002 |
| WO | WO 02/071977 A2 | 9/2002 |
| WO | WO 02/087481 A1 | 11/2002 |
| WO | WO 03/007778 | 1/2003 |
| WO | WO 03/043507 A2 | 5/2003 |
| WO | WO 03/073961 A1 | 9/2003 |
| WO | WO 03/090716 A1 | 11/2003 |
| WO | WO 03/099300 A1 | 12/2003 |
| WO | WO 03/099320 A1 | 12/2003 |

(56) References Cited

FOREIGN PATENT DOCUMENTS

| WO | WO 03/103538 A1 | 12/2003 |
|---|---|---|
| WO | WO 03/103743 A2 | 12/2003 |
| WO | WO 2004/012629 | 2/2004 |
| WO | WO 2004/019866 A2 | 3/2004 |
| WO | WO 2004/066805 A2 | 8/2004 |
| WO | WO 2004/100803 A1 | 11/2004 |
| WO | WO 2005/007031 | 1/2005 |
| WO | WO 2005/007873 A2 | 1/2005 |
| WO | WO 2005/041745 A2 | 5/2005 |
| WO | WO 2005/091860 A2 | 10/2005 |
| WO | WO 2005/102181 A1 | 11/2005 |
| WO | WO 2006/033107 A2 | 3/2006 |
| WO | WO 2006/055683 A2 | 5/2006 |
| WO | WO 2007/016349 A2 | 2/2007 |
| WO | WO 2007/092354 | 8/2007 |
| WO | WO 2007/143560 A2 | 12/2007 |
| WO | WO 2008/010792 A1 | 1/2008 |
| WO | WO 2011/011641 A2 | 1/2011 |
| WO | WO2012/099418 A2 | 7/2012 |
| WO | WO2013065036 A2 | 5/2013 |
| WO | WO 2013/128461 A1 | 9/2013 |

OTHER PUBLICATIONS

Nikolic et al.; U.S. Appl. No. 13/973,868 entitled "Therapeutic Methods and Devices Following Myocardial Infarction," filed Aug. 22, 2013.
Anand et al.; Isolated myocyte contractile function is normal in postinfarct remodeled rat heart with systolic dysfunction; Circulation; 96(11); pp. 3974-84; Dec. 1997.
Bozdag-Turan et al.; Left ventricular partitioning device in a patient with chronic heart failure: Short-term clinical follow-up; Int J Cardiol; 163(1); pp. e1 -e3; (Epub) Jul. 2012.
Dang et al.; Akinetic myocardial infarcts must contain contracting myocytes: finite-element model study; Am J Physiol Heart Circ Physiol ; 288; pp. H1844-H1850; Apr. 2005.
Dang et al.; Effect of ventricular size and patch stiffness in surgical anterior ventricular restoration: a finite element model study; Ann Thorac Surg; 79; pp. 185-193; Jan. 2005.
Grossman et al.; Wall stress and patterns of hypertrophy in the human left ventricle; J Clin Invest; 56; pp. 56-64; Jul. 1975.
Guccione et al.; Finite element stress analysis of left ventricular mechanics in the beating dog heart; J Biomech; 28; pp. 1167-1177; Oct. 1995.
Guccione et al.; Mechanics of active contraction in cardiac muscle: Part II—Cylindrical models of the systolic left ventricle; J Biomech Eng; 115; pp. 82-90; Feb. 1993.
Gutberlet et al.; Myocardial viability assessment in patients with highly impaired left ventricular function: comparison of delayed enhancement, dobutamine stress MRI, end-diastolic wall thickness, and TI201-SPECT with functional recovery after revascularization; Eur Radiol; 15; pp. 872-80; May 2005.
Huisman et al.; Measurement of left ventricular wall stress; Cardiovascular Research; 14; pp. 142-153; Mar. 1980.
Jackson et al.; Extension of borderzone myocardium in postinfarction dilated cardiomyopathy; J Am Coll Cardiol; 40(6); 1160-7; and discussion; pp. 1168-1171; Sep. 2002.
Jones et al.; Coronary Bypass Surgery with or without Surgical Ventricular Reconstruction; N Engl J Med; 360; pp. 1705-1717; Apr. 2009.
Lee et al.; A novel method for quantifying in-vivo regional left ventricular myocardial contractility in the border zone of a myocardial infarction (author manuscript, 11 pgs.); J Biomech Eng; 133; 094506; Sep. 2011.
Mazzaferri et al.; Percutaneous left ventricular partitioning in patients with chronic heart failure and a prior anterior myocardial infarction: Results of the Percutaneous Ventricular Restoration in Chronic Heart Failure Patients Trial; Am Heart J; 163; pp. 812-820; May 2012.

Nikolic et al.; Percutaneous implantation of an intraventricular device for the treatment of heart failure: experimental results and proof of concept; J Card Fail; 15(9); pp. 790-797; Nov. 2009.
Priola et al.; Functional characteristics of the left ventricular inflow and and outflow tracts; Circ Res; 17; pp. 123-129; Aug. 1965.
Sagic et al.; Percutaneous implantation of the left ventricular partitioning device for chronic heart failure: a pilot study with 1-year follow-up. Eur J Heart Fail; 12; pp. 600-606; Apr. 2010.
Sun et al.; A computationally efficient formal optimization of regional myocardial contractility in a sheep with left ventricular aneurysm (author manuscript, 21 pgs.); J Biomech Eng; 131; 111001; Nov. 2009.
Walker et al; Magnetic resonance imaging-based finite element stress analysis after linear repair of left ventricular aneurysm (author manuscript, 17 pgs.); J Thorac Cardiovasc Surg; 135; pp. 1094-1102 e1-2; May 2008.
Walker et al; MRI-based finite-element analysis of left ventricular aneurysm; Am J Physiol Heart Circ Physiol; 289; pp. H692-H700; Aug. 2005.
Walmsley; Anatomy of left ventricular outflow tract; British Heart Journal; 41; pp. 263-267; Mar. 1979.
Wenk et al.; First evidence of depressed contractility in the border zone of a human myocardial infarction; Ann Thorac Surg; 93; pp. 1188-1193; Apr. 2012.
Wenk et al.; Regional left ventricular myocardial contractility and stress in a finite element model of posterobasal myocardial infarction (author manuscript, pgs.); J Biomech Eng; 133(4); 044501; Apr. 2011.
Alexander et al.; U.S. Appl. No. 14/189,856 entitled "Systems and methods for improving cardiac function," filed Feb. 25, 2014.
Khairkhahan et al.; U.S. Appl. No. 14/681,930 entitled "Retrievable cardiac devices," filed Apr. 8, 2015.
Kermode et al.; U.S. Appl. No. 13/828,184 entitled "Devices and methods for delivering an endocardial device," filed Mar. 14, 2013.
AGA Medical Corporation. www.amplatzer.com/products. "The Muscular VSD Occluder" and "The Septal Occluder" device description. Accessed Apr. 3, 2002.
Artrip et al.; Left ventricular volume reduction surgery for heart failure: A physiologic perspective; J Thorac Cardiovasc Surg; vol. 122; No. 4; pp. 775-782; Oct. 2001.
Boersma et al.; Early thrombolytic treatment in acute myocardial infarction: reappraisal of the golden hour; Lancet: vol. 348(9030); pp. 771-775; Sep. 21, 1996.
Di Mattia, et al. Surgical treatment of left ventricular post-infarction aneurysm with endoventriculoplasty: late clinical and functioal results. European Journal of Cardio-thoracic Surgery. 15(4):413-418; Apr. 1999.
Dor, et al. Ventricular remodeling in coronary artery disease. Current Opinion in Cardiology. 12(6):533-537; Nov. 1997.
Dor, V. The treatment of refractory ischemic ventricular tachycardia by endoventricular patch plasty reconstruction of the left ventricle. Seminars in Thoracic and Cardiovascular Surgery. 9(2): 146-155; Apr. 1997.
Dor. Surgery for left ventricular aneurysm. Current Opinion in Cardiology. vol. 5; No. 6; pp. 773-780; Dec. 1990.
Gore Medical. www.goremedical.com. "Helex Septal Occluder" product description. Accessed Apr. 3, 2002.
James et al.; Blood volume and Brain Natriuretic Peptide in Congestive Heart Failure: A Pilot Study; American Heart Journal; vol. 150; issue 5, pp. 984.e1-984.e6 (abstract); Dec. 6, 2005.
Januzzi, James L.; Natriuretic peptide testing: A window into the diagnosis and prognosis of heart failure; Cleveland Clinic Journal of Medicine; vol. 73; No. 2; pp. 149-152 and 155-157; Feb. 2006.
Katsumata, et al. An objective appraisal of partial left ventriculectomy for heart failure. Journal of Congestive Heart Failure and Circulator Support. 1(2): 97-106; (year of pub. sufficiently earlier than effective US filing date and any foreign priority date) 1999.
Kawata, et al. Systolic and Diastolic Function after Patch Reconstruction of Left Ventricular Aneurysms. Ann. Thorac. Surg. 5(2)9:403-407; Feb. 1995.
Sharkey et al.; Left ventricular apex occluder. Description of a a ventricular partitioning device; EuroInterv.; 2(1); pp. 125-127; May 2006.

(56) References Cited

OTHER PUBLICATIONS

U.S. Food & Drug Administration; AneuRx Stent Graft System—Instructions for use; (pre-market approval); Sep. 29, 1999; downloaded Apr. 25, 2013 (http://www.accessdata.fda.gov/cdrh_docs/pdf/P990020c.pdf).

Boutillette et al.; U.S. Appl. No. 14/731,161 entitled "Devices and methods for delivering an endocardial device," filed Jun. 4, 2015.

Sojitra et al.; Electropolishing of 316LVM stainless steel cardiovascular stents: an investigation of material removal, surface roughness and corrosion behaviour; Trends Biomater. Artif. Organs; 23(3); pp. 115-121; (year of pub. sufficiently earlier than effective US filing date and any foreign priority date) 2010.

METHOD FOR MAKING A LAMINAR VENTRICULAR PARTITIONING DEVICE

CROSS-REFERENCE TO RELATED APPLICATIONS

This patent application claims priority as a continuation-in-part of U.S. patent application Ser. No. 12/893,832, filed on Sep. 29, 2010 (which is issued as U.S. Pat. No. 9,078,660 issued on Jul. 14 2015), which is a continuation-in-part of U.S. patent application Ser. No. 11/860,438, filed on Sep. 24, 2007 (which issued as U.S. Pat. No. 7,897,086 on Mar. 1, 2011), which is a continuation-in-part of U.S. patent application Ser. No. 10/913,608, filed on Aug. 5, 2004 (now abandoned). Each of these patent applications is herein incorporated by reference in their entirety.

U.S. patent application Ser. No. 12/893,832, filed on Sep. 29, 2010 also claims priority as a continuation-in-part of U.S. patent application Ser. No. 12/509,289, filed on Jul. 24, 2009, which is a continuation of U.S. patent application Ser. No. 11/151,164, filed on Jun. 10, 2005 (which issued as U.S. Pat. No. 7,582,051 on Sep. 1, 2009). U.S. patent application Ser. No. 12/893,832 also claims priority to U.S. provisional patent application Ser. No. 61/246,920, filed Sep. 29, 2009. Each of these patent applications is herein incorporated by reference in their entirety.

INCORPORATION BY REFERENCE

All publications and patent applications mentioned in this specification are herein incorporated by reference in their entirety, as if each individual publication or patent application was specifically and individually indicated to be incorporated by reference in its entirety.

TECHNICAL FIELD

The present invention relates generally to the field of treating heart diseases and more specifically, to a device and method for making a laminar ventricular partitioning device.

BACKGROUND

Congestive heart failure (CHF), characterized by a progressive enlargement of the heart, particularly the left ventricle, is a major cause of death and disability in the United States and elsewhere. As a patient's heart enlarges, it pumps less efficiently and, in time, the heart becomes so enlarged that it cannot adequately supply blood to the body. The fraction of blood within the left ventricle that is pumped forward at each stroke, commonly referred to as the "ejection fraction", is typically about sixty percent for a healthy heart. A congestive heart failure patient typically has an ejection fraction of 40% or less, and as a consequence, is chronically fatigued, physically disabled, and burdened with pain and discomfort. Further, as the heart enlarges, heart valves lose the ability to close adequately. An incompetent mitral valve allows regurgitation of blood from the left ventricle back into the left atrium, further reducing the heart's ability to pump blood.

Congestive heart failure can result from a variety of conditions, including viral infections, incompetent heart valves, ischemic conditions in the heart wall, or a combination of these conditions. Prolonged ischemia and occlusion of coronary arteries can result in myocardial tissue in the ventricular wall dying and becoming scar tissue. Once a portion of myocardial tissue dies, that portion no longer contributes to the pumping action of the heart. As the disease progresses, a local area of compromised myocardium can bulge during the heart contractions, further decreasing the heart's ability to pump blood, and further reducing the ejection fraction.

In the early stages of congestive heart failure, drug therapy is presently the most commonly prescribed treatment. Drug therapy typically treats the symptoms of the disease and may slow the progression of the disease, but it does not cure the disease. Presently, the only treatment considered curative for congestive heart disease is heart transplantation, but these procedures are high risk, invasive, and costly. Further, there is a shortage of hearts available for transplant, many patients fail to meet transplant-recipient qualifying criteria.

Much effort has been directed toward the development of surgical and device-based treatments for congestive heart disease. Surgical procedures have been developed to dissect and remove weakened portions of the ventricular wall in order to reduce heart volume. As is the case with heart transplant, these procedures are invasive, risky, and costly, and many patients do not qualify medically for the procedure. Other efforts to treat CHF include the use of an elastic support placed around the heart to prevent further deleterious remodeling, and mechanical assist devices and completely mechanical hearts have been developed. Recently, improvements have been made in treating patients with CHF by implanting pacing leads in both sides of the heart in order to coordinate the contraction of both ventricles of the heart. While these various procedures and devices have been found to be successful in providing some relief from CHF symptoms and in slowing disease progression, none has been able to stop the course of the disease.

SUMMARY

The present invention relates to a ventricular partitioning device and a method of employing the device in the treatment of a patient with congestive heart failure (CHF). Embodiments of the device are adapted to span a chamber of the heart, typically the left ventricle, and partition the chamber into a main productive portion and a secondary non-productive portion. This partitioning reduces the total volume of the heart chamber, reduces the stress applied to the heart and, as a result, improves the blood ejection fraction thereof.

Embodiments of the device have a reinforced partitioning component with a concave, pressure-receiving surface which, in part, defines the main productive portion of the partitioned heart chamber when secured therein. The reinforced partitioning component preferably includes a hub and a membrane forming the pressure receiving surface. The partitioning component is reinforced by a radially expandable frame component formed of a plurality of ribs.

The ribs of the expandable frame have distal ends secured to the central hub and free proximal ends. The distal ends are preferably secured to the central hub to facilitate radial self expansion of the free proximal ends of the ribs away from a centerline axis. The distal ends of the ribs may be pivotally mounted to the hub and biased outwardly or fixed to the hub. The ribs may be formed of material such as superelastic NiTi alloy that permits compression if the free proximal ends of the ribs toward a centerline axis into a contracted configuration, and when released, allows for their self expansion to an expanded configuration.

The free proximal ends of the ribs are configured to engage and preferably penetrate the tissue lining a heart chamber, typically the left ventricle, to be partitioned so as to secure the peripheral edge of the partitioning component to the heart wall and to fix the partitioning component within the chamber so as to partition the chamber in a desired manner. The tissue-penetrating proximal tips are configured to penetrate the tissue lining at an angle approximately perpendicular to a center line axis of the partitioning device. The tissue penetrating proximal tips of the ribs may be provided with attachments such as barbs or hooks that prevent withdrawal of the tips from the heart wall.

The ribs in their expanded configuration angle outwardly from the hub and the free proximal ends curve outwardly so that the membrane secured to the ribs of the expanded frame forms a trumpet-shaped, pressure receiving surface. The partitioning membrane in the expanded configuration has radial dimensions from about 10 to about 160 mm, preferably about 50 to about 100 mm, as measured from the center line axis.

The partitioning device may be delivered percutaneously or intraoperatively. One particularly suitable delivery catheter has an elongated shaft, a releasable securing device on the distal end of the shaft for holding the partitioning device on the distal end, and an expandable member such as an inflatable balloon on a distal portion of the shaft proximal to the distal end to press the interior of the recess formed by the pressure-receiving surface to ensure that the tissue penetrating tips or elements on the periphery of the partitioning device penetrate sufficiently into the heart wall to hold the partitioning device in a desired position to effectively partition the heart chamber.

More particularly, the invention relates to an intracorporeal partitioning component that includes a frame with a plurality of ribs that is integrated with one or more sheets of fabric to form a unified unilaminar, bilaminar, or multilaminar structure, as well as methods for making the partitioning component. Embodiments of the invention thus include an intra partitioning component that includes a frame having a plurality of ribs with radially extending proximal ends and with distal ends secured to a hub; and a bilaminar sheet secured to the ribs of the frame by fused thermoplastic material within the bilaminar sheet of material. In some of these embodiments, the bilaminar sheet of material comprises ePTFE. In some embodiments, the bilaminar sheet includes a porous material; in other embodiments the bilaminar sheet includes a non-porous material.

Embodiments of the invention further include an intracorporeal partitioning component that includes a frame having a plurality of ribs with radially extending proximal ends and with distal ends secured to a hub; and a single sheet secured to the ribs of the frame by fused thermoplastic material on one side of the sheet of material to form a unilaminar structure.

Embodiments of the invention also include an intracorporeal product that includes a first component configured for intracorporeal deployment, the component encased in thermoplastic material; and at least two sheets of ePTFE material secured to the first component by fused thermoplastic material therebetween to form at least a bilaminar sheet of ePTFE material.

Embodiments of the invention include a method of securing a polymeric sheet material to rib components of a frame structure, including disposing a tube comprising thermoplastic material over each of one or more rib components of the frame to form a thermoplastic-material-encased rib; forming an assembly by applying the thermoplastic-encased rib above a first sheet and a second sheet above the thermoplastic-encased rib; and heating the assembly to fuse the first and second sheets to the thermoplastic material to form a bilaminar sheet, the fusion occurring by the melting and reforming of the thermoplastic material between the sheets, the rib remaining within the melted and reformed thermoplastic material. These embodiments include methods wherein the first sheet and second sheet of material include ePTFE. In other embodiments, the first sheet and second sheet of material include a porous material. And in still other embodiments, the first sheet and second sheets of material may include a porous material, and the other of the first sheet and second sheets may include a nonporous material.

In some of these method embodiments, the heating includes exposure to a temperature of about 500.degree. F., and in some of these embodiments the heating occurs over a period of about 120 seconds. In some of these embodiments, the method further includes applying pressure to the assembly to fuse the thermoplastic material and the ePTFE sheets to the rib component, such applied pressure being between about 60 psi and about 90 psi. And in some of these embodiments wherein the pressure is applied for a period of about 120 seconds.

Some embodiments of the invention include a method of making an intracorporeal product, including: (a) providing two ePTFE sheets; (b) providing a rib component of a frame structure; (c) deploying a thermoplastic-material containing element over at least part of the rib component; (d) applying the ePTFE sheets to at least a portion of the rib component covered by the thermoplastic element, the rib component disposed between the sheets, to form an assembly; and (e) heating the assembly to fuse the thermoplastic material and the ePTFE sheets to the rib component, the ePTFE sheets thereby forming a bilaminar ePTFE sheet structure secured to the rib component. In various of these embodiments, the heating step includes exposure to a temperature ranging between about 260.degree. F. and about 530.degree. F. More particularly, the heating may include exposure to a temperature ranging between about 375.degree. F. and about 520.degree. F. Still more particularly, the heating may include exposure to a temperature ranging between about 490.degree. F. and about 510.degree. F. And in some embodiments, the heating may include exposure to a temperature of about 500.degree. F.

Some embodiments of the method of making an intracorporeal product further include applying pressure to the assembly to fuse the thermoplastic material and the ePTFE sheets to the rib component. In some of these embodiments, the pressure applied is between about 10 psi and about 150 psi. In some particular embodiments, the pressure applied is between about 35 psi and about 120 psi. And in some particular embodiments, the pressure applied is between about 60 psi and about 90 psi.

Some embodiments of the method of making an intracorporeal product include applying heat and pressure to the assembly for a predetermined period of time that ranges between about 30 seconds and about 360 seconds. In some embodiments, the period of time ranges between about 75 seconds and about 240 seconds. And in some particular embodiments, the period of time is about 120 seconds.

Some embodiments of the method of making an intracorporeal product the fusion of polyethylene material and poly-tetra-fluoro-ethylene (PTFE) material occurs by the polyethylene melting and intercalating into the ePTFE fabric, cooling, and reforming to create interlocking zones of material continuity between polyethylene and polytetrafluoroethylene (PTFE).

Some embodiments of the method of making an intracorporeal product include (a) providing one ePTFE sheet; (b) providing a rib component of a frame structure; (c) deploying a thermoplastic-material containing element over at least part of the rib component; (d) applying the ePTFE sheet to at least a portion of the rib component covered by the thermoplastic element, the rib component disposed adjacent to the sheet, to form an assembly; and (e) heating the assembly to fuse the thermoplastic material and the ePTFE sheets to the rib component, the ePTFE sheet thereby forming a unilaminar ePTFE sheet structure secured to the rib component.

Also described herein is a method of securing a polymeric sheet to rib components of a frame structure, wherein the rib components are jointed at a hub to form an expandable and collapsible implant. In general, the method may include the steps of disposing a tube comprising thermoplastic material over each of one or more rib components of the frame; forming an assembly by applying the thermoplastic-encased rib adjacent to at least one polymeric sheet of material; and heating the assembly to fuse the sheet to the thermoplastic material to form a fused sheet, the fusion occurring by the heating and reforming of the thermoplastic material to the sheet, the rib remaining within the reformed thermoplastic material, wherein the implant is adapted to span a left ventricle. In some embodiments, the method further includes the step applying pressure to the assembly to form a fused sheet.

In some embodiments, the disposing step may further include forming a thermoplastic-material-encased rib. In some embodiments, the disposing step may further include forming thermoplastic-material-encased ribs having proximal portions that are not encased in the thermoplastic material. In some embodiments, the disposing step may further include forming thermoplastic-material-encased ribs having tissue-penetrating proximal ends that are not encased in the thermoplastic material. In some embodiments, the disposing step may further include forming thermoplastic-material-encased ribs, wherein the thermoplastic material is disposed over a first portion of a first rib and a second portion of a second rib, wherein the first and second ribs are adjacent to one another and the first portion is at a different position along the length of the rib than the second portion.

In some embodiments, at least one polymeric sheet of material comprises ePTFE. In some embodiments, the fused sheet is a unilaminar sheet.

Also described herein are methods of securing a polymeric sheet to rib components of a frame structure, wherein the rib components are jointed at a hub to form an expandable and collapsible implant, wherein the implant is adapted to span a left ventricle. In general, the method includes the steps of providing an assembly, the assembly comprising a frame structure disposed between a first and second polymeric sheet; and heating the assembly under pressure to fuse the first polymeric sheet to the second polymeric sheet around the frame structure to form a fused sheet. In some embodiments, the first and second polymeric sheets comprise ePTFE.

Also described herein are methods for securing a polymeric sheet to rib components of a frame structure, wherein the rib components are jointed at a hub to form an expandable and collapsible implant. In general the method may include the steps of decreasing a diameter of the frame structure; placing the frame structure into an assembly fixture, wherein the assembly fixture is configured to hold the frame structure in a loaded configuration with a decreased diameter; placing a polymeric sheet into the assembly fixture; and heating the assembly under pressure to fuse the sheet to the frame structure.

In some embodiments, the method further includes the step of disposing a tube comprising thermoplastic material over each of one or more rib components of the frame. In some embodiments, the method further includes the step of forming an assembly by applying the thermoplastic-encased rib adjacent to at least one polymeric sheet of material. In some embodiments, the fusion occurs by the heating and reforming of the thermoplastic material to the sheet.

Also described herein is an assembly fixture for securing a polymeric sheet to rib components of a frame structure, wherein the rib components are jointed at a hub to form an expandable and collapsible implant. In general, the fixture may include a first platen having male shaping portion and a rim portion positioned around the periphery of the first platen; and a second platen having female shaping portion and a rim portion positioned around the periphery of the second platen; wherein the male and female shaping portions are configured to hold the rib components of the frame structure in a loaded configuration with a decreased diameter.

In some embodiments, the male and female shaping portions have complimentary curved shapes configured to hold the frame in a curved, loaded configuration with a decreased diameter.

In some embodiments, the two rim portions form complementary planar surfaces which serve to hold edges of the polymeric sheet. In some embodiments, the male and female shaping portions are further configured to press the polymeric sheet. In some embodiments, the polymeric sheet comprises ePTFE.

BRIEF DESCRIPTION OF THE DRAWINGS

FIG. 14A shows an exploded and partially cutaway view of the components of the device assembled for lamination; FIG. 14B provides of cutaway view of the device within a press, the press in a closed position; FIG. 14C shows a perspective view of an exemplary device; FIG. 14D provides a frontal view of the device after assembly.

FIG. 15A shows an exploded and partially cutaway view of the components of the device assembled for lamination; FIG. 15B provides of cutaway view of the device within the press in a closed position; FIG. 15C shows a perspective view of an exemplary device; and FIG. 15D provides a frontal view of the device after assembly.

FIG. 16 provides cross-sectional views of an assembly from which a bilaminar partitioning device is formed.

FIG. 17 provides cross-sectional views of an assembly from which a bilaminar partitioning device is formed.

FIG. 18 provides cross-sectional views of an assembly from which a unilaminar partitioning device is formed.

FIG. 19 provides cross-sectional views of an assembly from which a unilaminar partitioning device is formed.

FIGS. 22-23B include a view of an assembly for the making of an intracorporeal partitioning device, as well as views of the assembled device. FIG. 22 shows an exploded and partially cutaway view of the components of the assembly for lamination; FIGS. 23A and 23B illustrate the assembled device.

DETAILED DESCRIPTION

Figure 1:
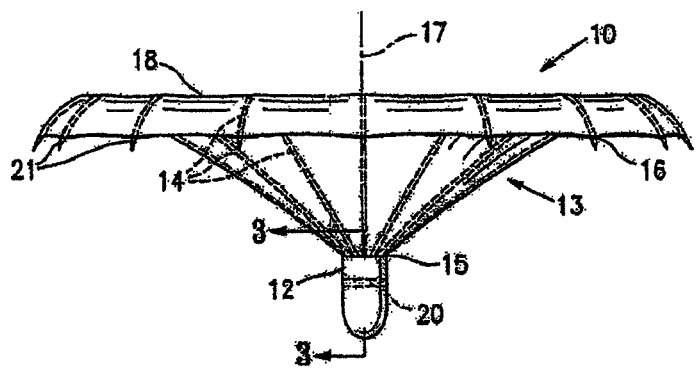
FIG. 1 is an elevational view of a partitioning device embodying features of the invention in an expanded configuration.

FIGS. 1-4 illustrate a partitioning component 10 which embodies features of the invention and which includes a partitioning membrane 11, a hub 12, preferably centrally located on the partitioning device, and a radially expandable reinforcing frame 13 formed of a plurality of ribs 14. Embodiments of the partitioning component 10 may be alternatively referred to as an intracorporeal partitioning component or an intracorporeal product, referring to its position within a ventricle of the heart, and to its function in partitioning the ventricle. Preferably, the partitioning membrane 11 is secured to the proximal or pressure side of the frame 13 as shown in FIG. 1. The ribs of the intracorporeal device 14 have distal ends 15 which are secured to the hub 12 and free proximal ends 16 which are configured to curve or flare away from a center line axis 17. Radial expansion of the free proximal ends 16 unfurls the membrane 11 secured to the frame 13 so that the membrane presents a relatively smooth, pressure receiving surface 18 which defines in part the productive portion of the patient's partitioned heart chamber.

Figure 3:
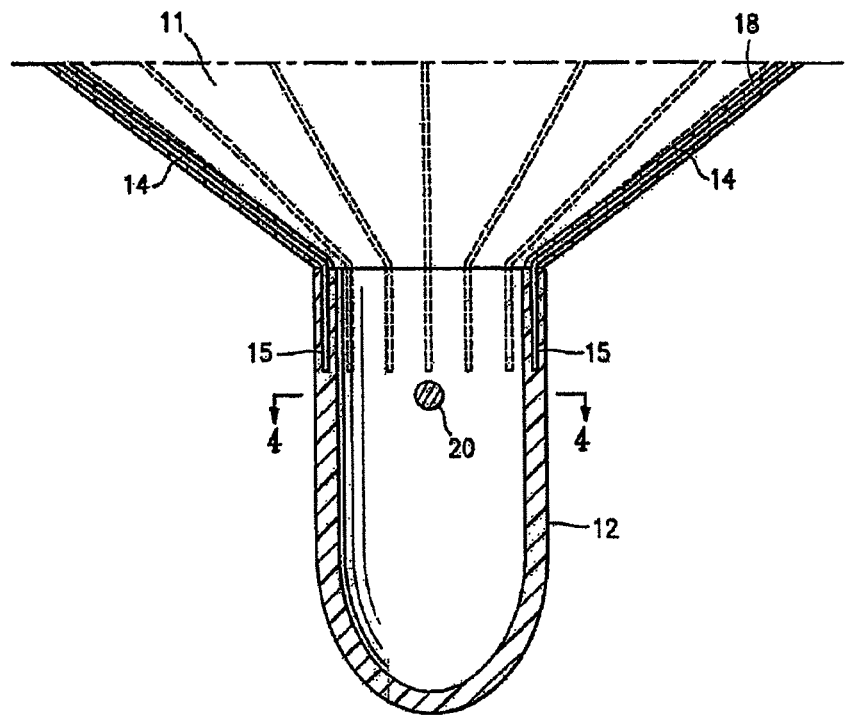
FIG. 3 is a partial longitudinal cross-sectional view of the hub of the partitioning device shown in FIG. 1.
Figure 4:
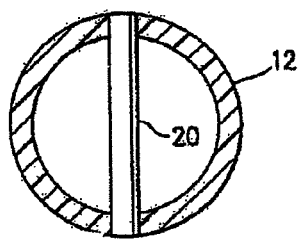
FIG. 4 is a transverse cross sectional view of the hub shown in FIG. 3 taken along the lines 4-4.
Figure 5:
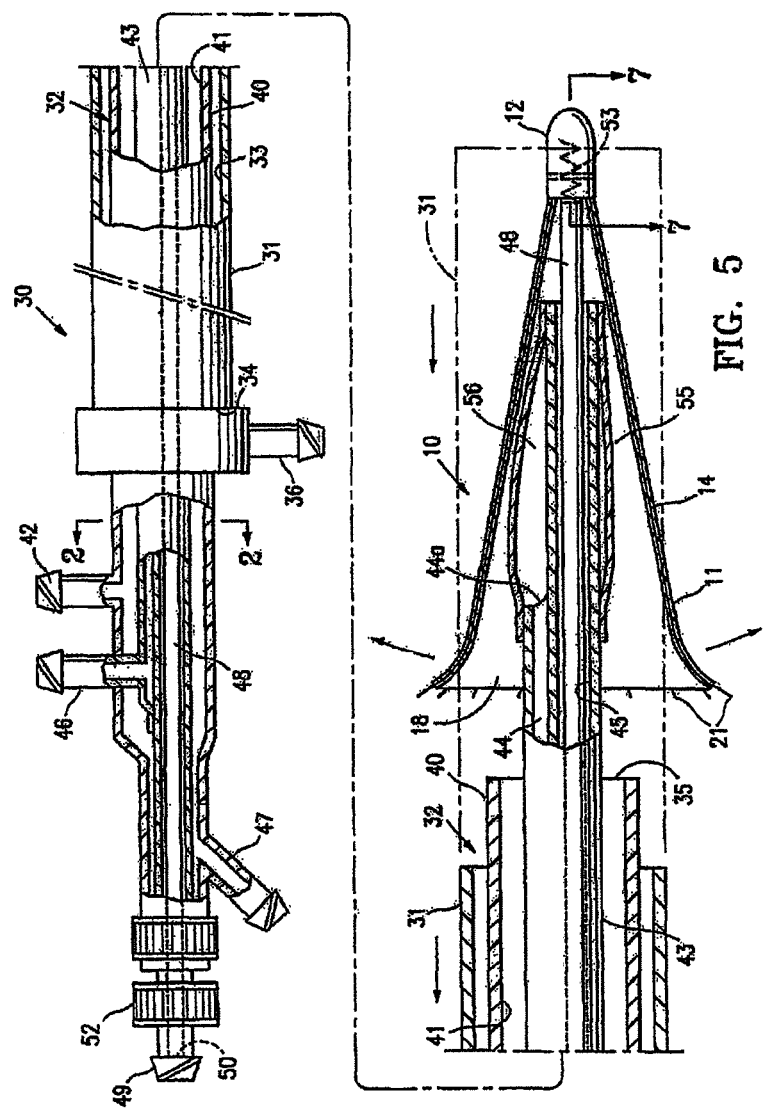
FIG. 5 is a schematic elevational view of a delivery system for the partitioning device shown in FIGS. 1 and 2.
Figure 6:
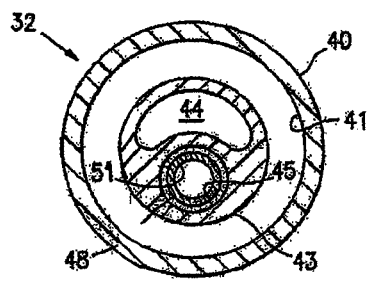
FIG. 6 is a transverse cross-sectional view of the delivery system shown in FIG. 5 taken along the lines 6-6.

As shown in more detail in FIGS. 3 and 4, the distal ends 15 of the ribs 14 are secured within the hub 12 and a transversely disposed connector bar 20 is secured within the hub which is configured to secure the hub 12 and thus the partitioning component 10 to a delivery system such as shown in FIGS. 5 and 6. The curved free proximal ends 16 of ribs 14 are provided with sharp tip elements 21 which are configured to hold the frame 13 and the membrane 11 secured thereto in a deployed position within the patient's heart chamber. Preferably, the sharp tip elements 21 of the frame 13 penetrate into tissue of the patient's heart wall in order to secure the partitioning component 10 within the heart chamber so as to partition the ventricular chamber into a productive portion and a non-productive portion.

The connector bar 20 of the hub 12, as will be described later, allows the partitioning device 10 to be secured to a delivery system and to be released from the delivery system within the patient's heart chamber. The distal ends 15 of the reinforcing ribs 14 are secured within the hub 12 in a suitable manner or they may be secured to the surface defining the inner lumen or they may be disposed within channels or bores in the wall of the hub 12. The ribs 14 are pre-shaped so that when not constrained other than by the membrane 11 secured thereto (as shown in FIGS. 1 and 2), the free proximal ends 16 thereof expand to a desired angular displacement away from a center line axis 17 which is about 20 degrees to about 90 degrees, preferably about 50 degrees to about 80 degrees.

Figure 2:
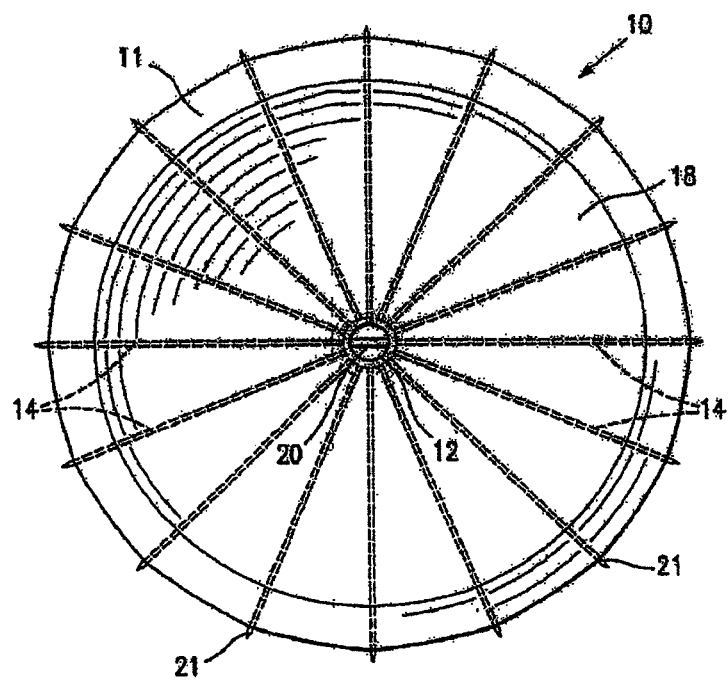
FIG. 2 is a plan view of the partitioning device shown in FIG. 1.
Figure 7:
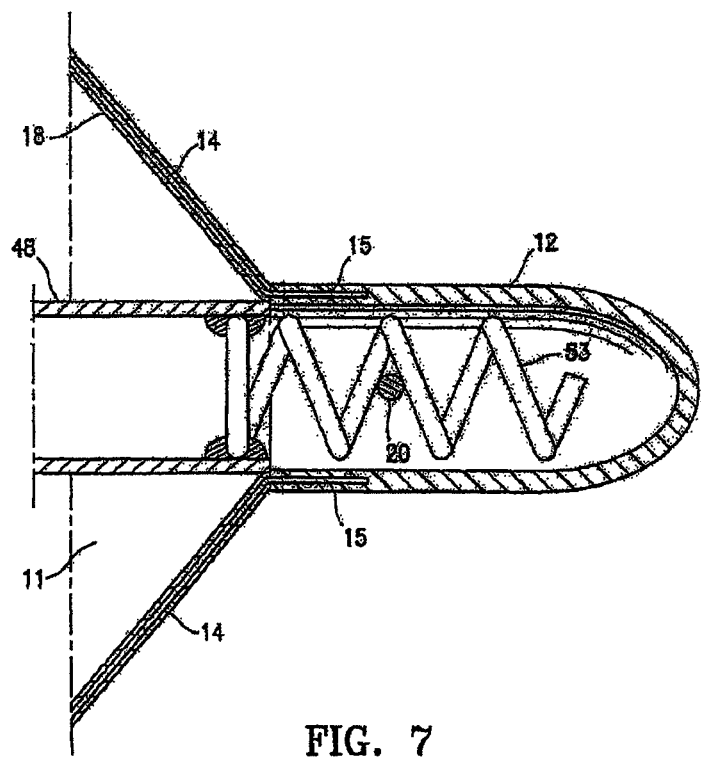
FIG. 7 is an elevational view, partially in section, of the hub shown in FIG. 3 secured to the helical coil of the delivery system shown in FIG. 5.

FIGS. 5-7 illustrate a suitable delivery system 30 delivering the partitioning component 10 shown in FIGS. 1 and 2 into a patient's heart chamber and deploying the partitioning component 10 to partition the heart chamber as shown in FIGS. 8A-8E. The delivery system 30 includes a guide catheter 31 and a delivery catheter 32.

The guide catheter has an inner lumen 33 extending between the proximal end 34 and distal end 35. A hemostatic valve (not shown) may be provided at the proximal end 34 of the guide catheter 31. A flush port 36 on the proximal end 34 of guide catheter 31 is in fluid communication with the inner lumen 33.

The delivery catheter 32 has an outer shaft 40 with an inner lumen 41 and a proximal injection port 42, an inner shaft 43 disposed within the inner lumen 41 with a first lumen 44 and a second lumen 45. Balloon inflation port 46 is in fluid communication with the first lumen 44 and flush port 47 is in fluid communication with the second lumen 45. Torque shaft 48 is rotatably disposed within the second lumen 44 of the inner shaft 43 and has an injection port 49 provided at its proximal end 50 in fluid communication with the inner lumen 51 of the torque shaft. The torque shaft 48 is preferably formed at least in part of a hypotube formed of suitable material such as superelastic Nitinol or stainless steel. A torque knob 52 is secured to the proximal end 50 of torque shaft 48 distal to the injection port 49. A helical coil screw 53 is secured to the distal end of the torque shaft 48 and rotation of the torque knob 52 on the proximal end 50 of the torque shaft 48 rotates the screw 53 on the distal end of torque shaft 48 to facilitate deployment of a partitioning device 10. An inflatable balloon 55 is sealingly secured to the distal end of the inner shaft 43 and has an interior 56 in fluid communication with the first lumen 44. Inflation fluid may be delivered to the interior 56 through port 44a in the portion of the inner shaft 43 extending through the balloon 55. Inflation of the balloon 55 by inflation fluid through port 46 facilitates securing the partitioning component 10.

To deliver the partitioning component 10, it is secured to the distal end of the delivery catheter 32 by means of the helical coil screw 53. The partitioning component 10 is collapsed to a first, delivery configuration which has small enough transverse dimensions to be slidably advanced through the inner lumen 33 of the guide catheter 31. Preferably, the guide catheter 31 has been previously percutaneously introduced and advanced through the patient's vasculature, such as the femoral artery, in a conventional manner to the desired heart chamber. The delivery catheter 32 with the partitioning component 10 attached is advanced through the inner lumen 33 of the guide catheter 31 until the partitioning component 10 is ready for deployment from the distal end of the guide catheter 31 into the patient's heart chamber 58 to be partitioned.

Figure 8A:
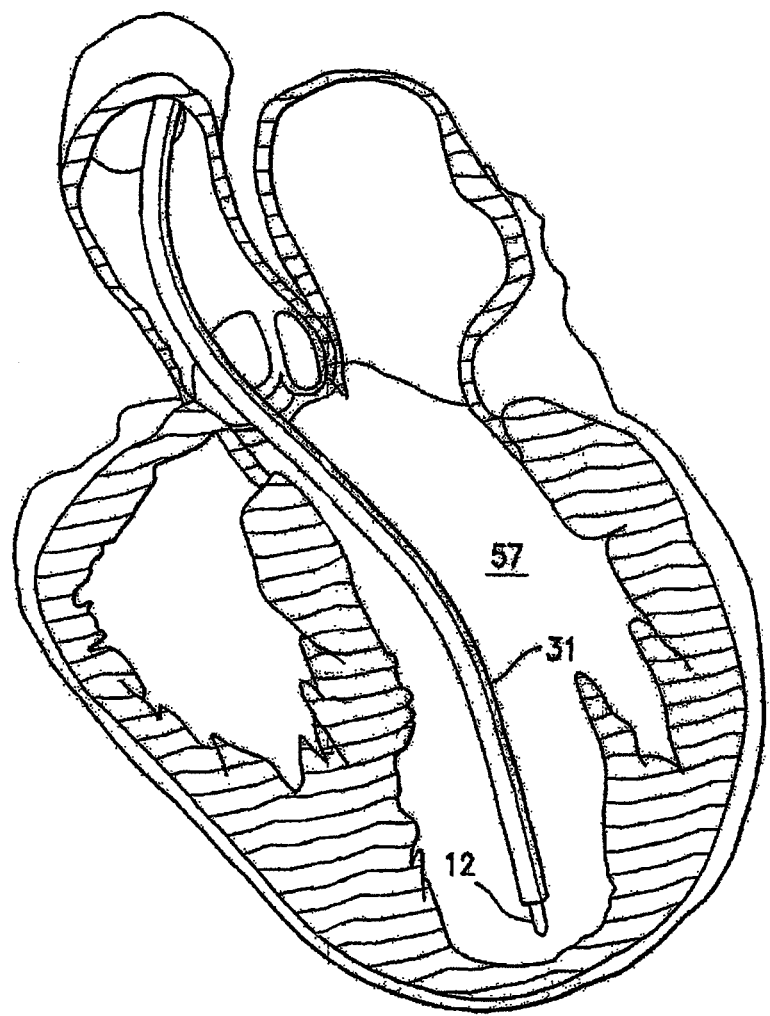
FIGS. 8A-8E are schematic views of a patient's left ventricular chamber illustrating the deployment of the partitioning device shown in FIGS. 1 and 2 with the delivery system shown in FIG. 5 to partition the heart chamber into a primary productive portion and a secondary, non-productive portion.
Figure 8B:
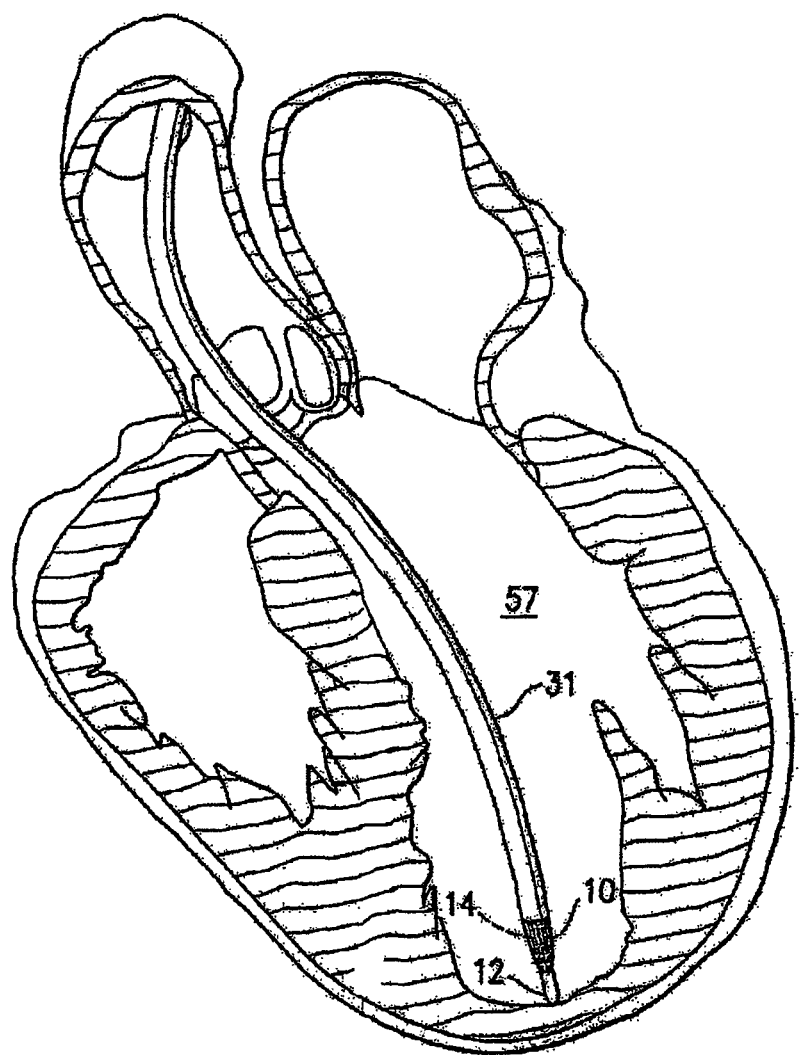
Figure 8C:
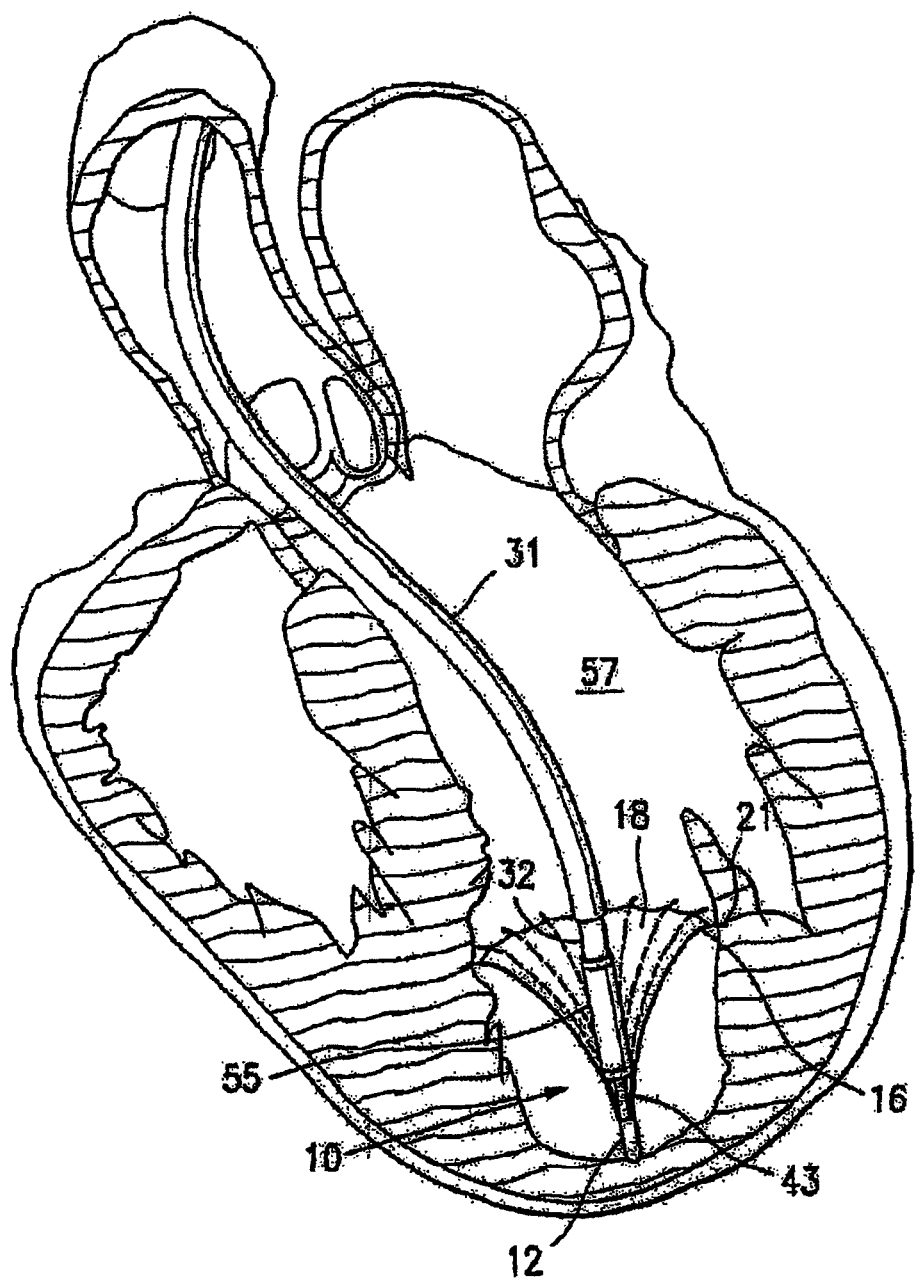
Figure 8D:
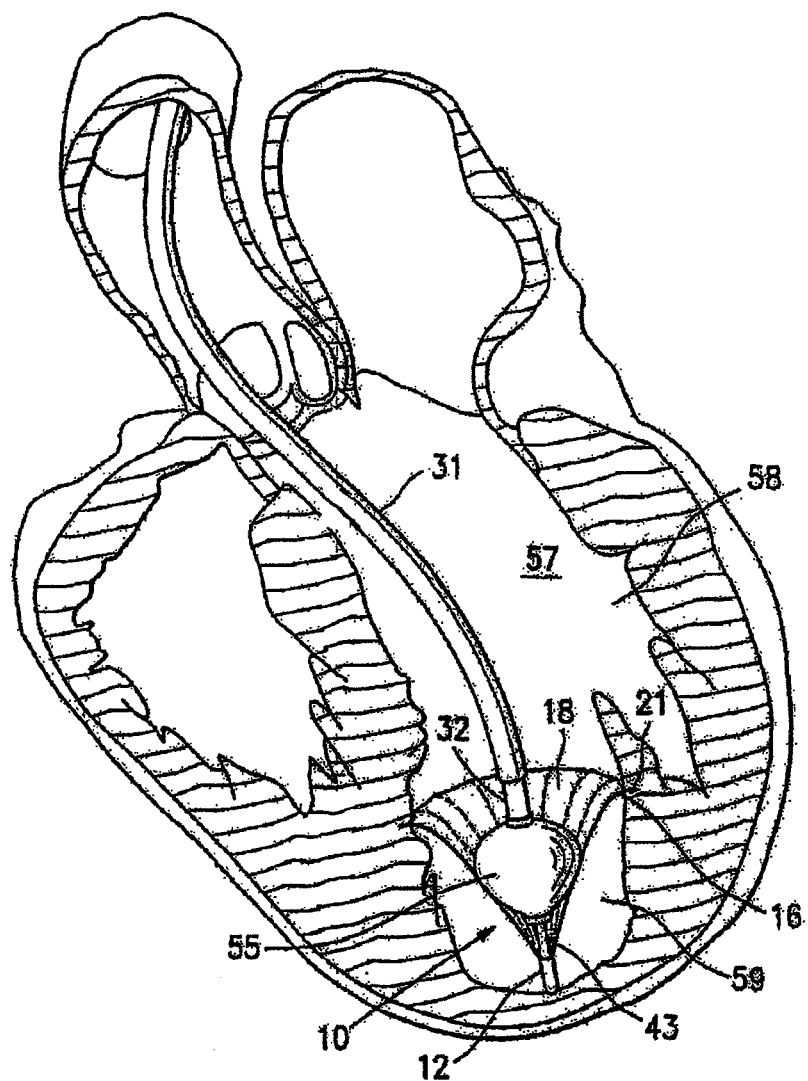
Figure 8E:
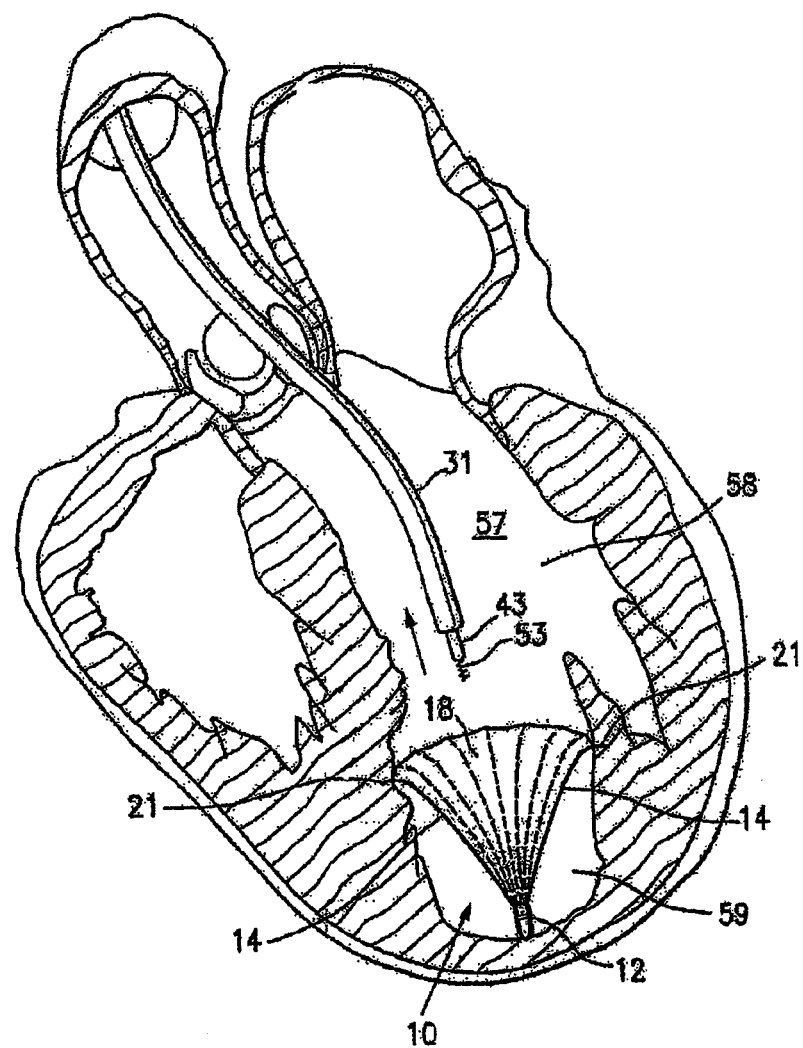

The partitioning component 10 mounted on the screw 53 is urged partially out of the inner lumen 33 of the guide catheter 31 until the hub 12 engages the heart wall as shown in FIG. 8B with the free proximal ends 16 of the ribs 14 in a contracted configuration within the guide catheter. The guiding catheter 31 is withdrawn while the delivery catheter 32 is held in place until the proximal ends 16 of the ribs 14 exit the distal end of the guiding catheter. The free proximal ends 16 of ribs 14 expand outwardly to press the sharp proximal tips 21 of the ribs 14 against and preferably into the tissue lining the heart chamber, as shown in FIG. 8C.

With the partitioning component deployed within the heart chamber and preferably partially secured therein, inflation fluid is introduced through the inflation port 46 into first lumen 44 of inner shaft 43 of the delivery catheter 32 where it is directed through port 44a into the balloon interior 56 to inflate the balloon. The inflated balloon presses against the pressure receiving surface 18 of the partitioning component 10 to ensure that the sharp proximal tips 21 are pressed well into the tissue lining the heart chamber.

With the partitioning device 10 properly positioned within the heart chamber, the knob 52 on the torque shaft 48 is rotated counter-clockwise to disengage the helical coil screw 53 of the delivery catheter 32 from the hub 12. The counter-clockwise rotation of the torque shaft 48 rotates the helical coil screw 53 which rides on the connector bar 20 secured within the hub 12. Once the helical coil screw 53 disengages the connector bar 20, the delivery system 30, including the guide catheter 31 and the delivery catheter 32, may then be removed from the patient.

The proximal end of the guide catheter 31 is provided with a flush port 36 to inject therapeutic or diagnostic fluids through the inner lumen 33. Similarly, the proximal end of the delivery catheter 32 is provided with a flush port 42 in communication with inner lumen 41 for essentially the same purpose. An inflation port 46 is provided on the proximal portion of the delivery catheter for delivery of inflation fluid through the first inner lumen 44 to the interior 56 of the balloon 55. Flush port 47 is provided in fluid communication with the second inner lumen 45 of the inner shaft 43. An injection port 49 is provided on the proximal end of the torque shaft 48 in fluid communication with the inner lumen 51 of the torque shaft for delivery of a variety of fluids.

The partitioning component 10 partitions the patient's heart chamber 57 into a main productive or operational portion 58 and a secondary, essentially non-productive portion 59. The operational portion 58 is much smaller than the original ventricular chamber 57 and provides for an improved ejection fraction. The partitioning increases the ejection fraction and provides an improvement in blood flow. Over time, the non-productive portion 59 fills first with thrombus and subsequently with cellular growth. Bio-resorbable fillers such as polylactic acid, polyglycolic acid, polycaprolactone, and copolymers and blends may be employed to initially fill the non-productive portion 59. Fillers may be suitably supplied in a suitable solvent such as DMSO. Other materials which accelerate tissue growth or thrombus may be deployed in the non-productive portion 59.

Figure 9:
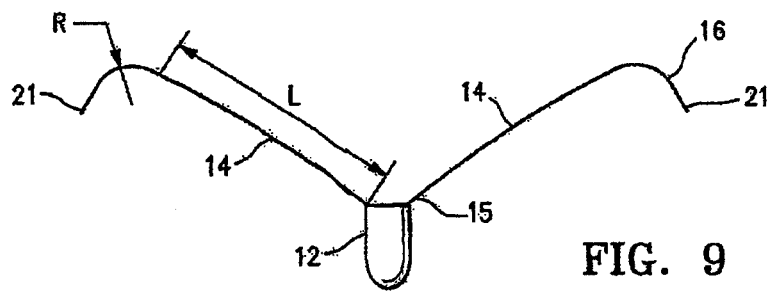
FIG. 9 is a partial schematic view of the expandable frame of the partitioning device shown in FIGS. 1 and 2 in an unrestricted configuration.
Figure 10:
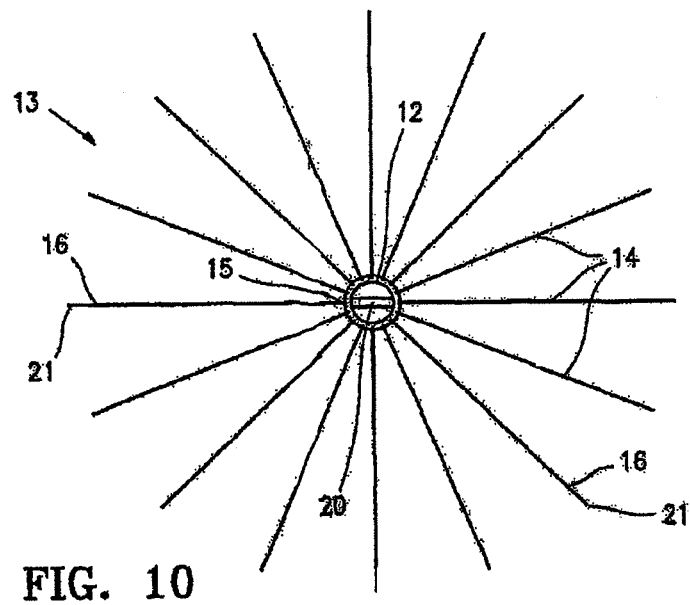
FIG. 10 is a top view of the expandable frame shown in FIG. 9.

FIGS. 9 and 10 illustrate the reinforcing frame 13 in an unstressed configuration and include the ribs 14 and the hub 12. The ribs 14 have a length L of about 1 to about 8 cm, preferably, about 1.5 to about 4 cm for most left ventricle deployments. The proximal ends 16 have a flared construction. To assist in properly locating the device during advancement and placement thereof into a patient's heart chamber, parts, e.g. the distal extremity, of one or more of the ribs and/or the hub may be provided with markers at desirable locations that provide enhanced visualization by eye, by ultrasound, by X-ray, or other imaging or visualization means. Radiopaque markers may be made with, for example, stainless steel, platinum, gold, iridium, tantalum, tungsten, silver, rhodium, nickel, bismuth, other radiopaque metals, and alloys and oxides of these metals.

Figure 11:
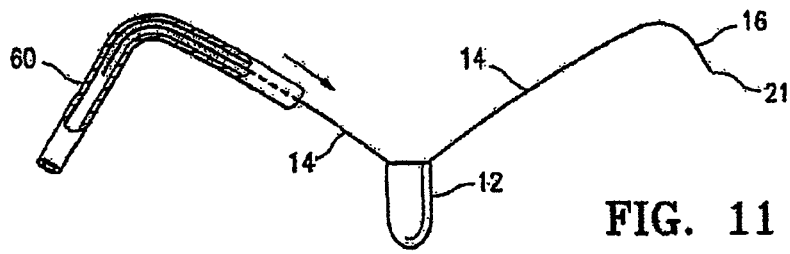
FIGS. 11 and 12 are schematic illustrations of a method of forming the partitioning device shown in FIGS. 1 and 2 from the expandable frame shown in FIGS. 9 and 10.
Figure 12:
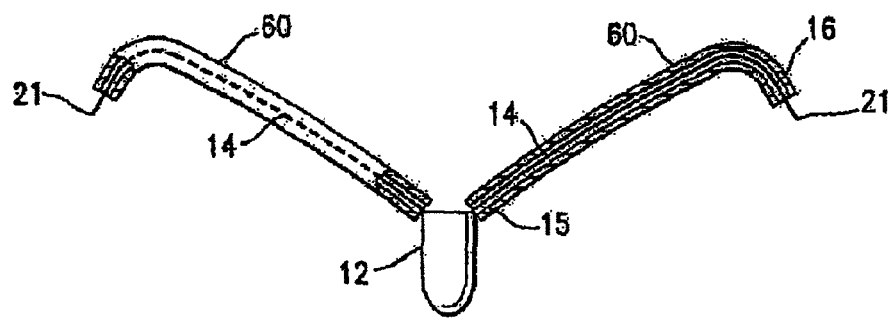
Figure 13:
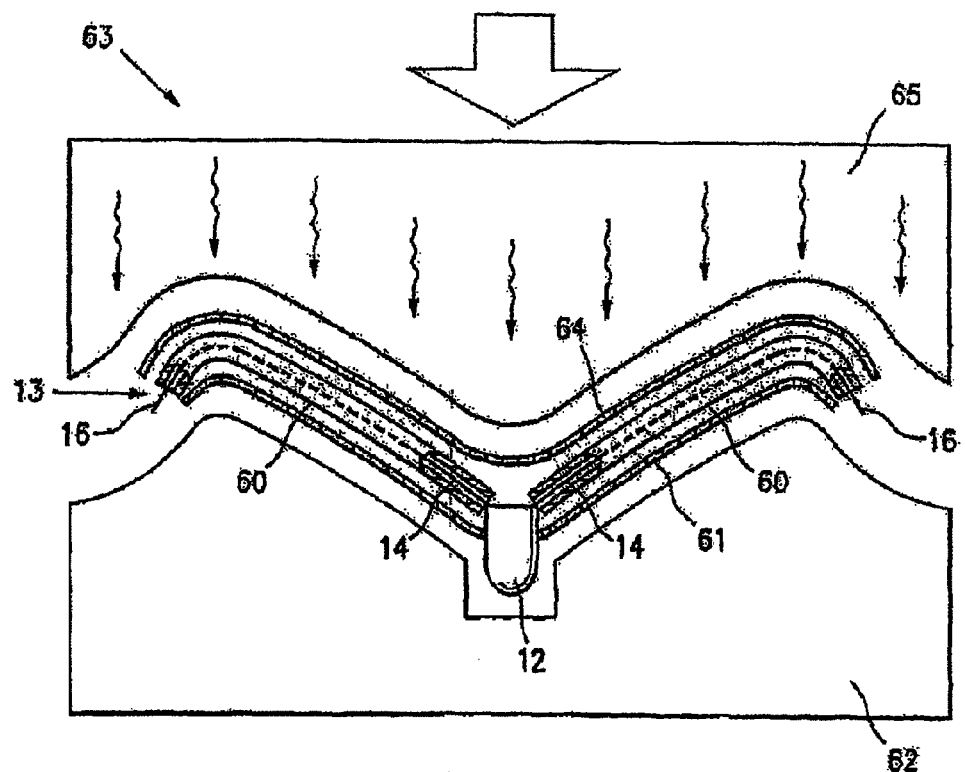
FIG. 13 is a schematic view of the assembled components shown in FIG. 12, as they are situated in a laminating press.

Embodiments of the partitioning device 10, both unilaminar and bilaminar embodiments, are conveniently formed by placing a thermoplastic tube 60, e.g. polyethylene or high density polyethylene (HDPE), over the ribs 14 of the frame 13 as shown in FIG. 11 until the proximal ends 16 of the ribs 14 extend out the ends of the thermoplastic tubes as shown in FIG. 12, to form thermoplastic-encased ribs. Further steps in the process of forming a unilaminar or bilaminar partitioning device make use of a press or lamination mold 63 that includes a female platen 62 and a male platen 65, one or both of which can be heated and cooled according to process specifics. A first expanded polytetrafluoroethylene (ePTFE) sheet 61 of appropriate size is placed in the female platen 62 of the mold or press 63. The frame 13, with tubes 60 slidably disposed or deployed over the ribs 14, is placed in platen 62 on top of the ePTFE sheet 61. In some alternative embodiments, the ePTFE sheet may be placed over the ribs. The center portion of the sheet 61 may be provided with an opening through which the hub 12 extends. In the case of forming a bilaminar embodiment, a second ePTFE sheet 64 is placed on top of the ribs 14 of frame 13 as shown in FIG. 13. The melting point of the thermoplastic material is lower than that of the ePTFE, thus the application of heat and pressure, as detailed below, is sufficient to melt the thermoplastic material but does not cause melting of the ePTFE.

Embodiments of methods to form a partitioning device that joins ePTFE sheet material, polyethylene material, and ribs into an integral structure include the application of heat and pressure. Heat and pressure may be applied through a mold or press 63 for a period of predetermined period of time, such as from about 30 seconds to about 360 seconds, or more particularly from about 75 seconds to about 240 seconds, or still more particularly, for about 120 seconds. Either the male platen 65 or the female platen 62, or both male and female platens may be heated so as to attain an operating temperature of between about 260.degree. F. and 530.degree. F., particularly to a temperature between about 375.degree. F. and 520.degree. F., and more particularly to temperature between about 490.degree. F. and about 510.degree. F., and still more particularly to a temperature of about 500.degree. F. In some embodiments, the assembly may be pressed (i.e., pressurized or pressurized), the applied pressure being in the range of about 10 psi to about 150 psi. In some particular embodiments, the pressure is between about 35 psi and about 120 psi, and in more particular embodiments, between about 60 psi and about 90 psi. In some embodiments, a single sheet of ePTFE is utilized to make a unilaminar device, the single sheet corresponding to the first sheet 61 of FIG. 13.

PTFE fabric is a woven material that varies with regard to the thickness of fibers and in the internodal distance between fibers. The presence of the space or volume between fibers provides the material with a foraminous quality which is advantageous for fusion or adhesion processes. Various forms of ePTFE have average internodal distances that vary from about one micron up to about 1,000 microns. Typical embodiments of ePTFE fabric appropriate for the manufacture of the herein described partitioning device may have internodal distances of between about 5 microns to about 200 microns, more particularly from about 10 microns to about 100 microns, and still more particularly from about 20 microns to about 50 microns. Aspects of the lamination process are described further below, and illustrated in FIGS. 14-21. Sheets may be formed of either porous or non-porous ePTFE, as well as other suitable biocompatible materials, as described further below.

As described further, below, the ePTFE fabric is typically stretched during the lamination process, under the conditions of heat and pressure that are applied by the press. Such stretching may not be uniform across the fabric surface, the maximal linear stretch in portions of the fabric may be of a magnitude of 2-fold to 4-fold. The stretching of fabric serves, in general terms, to reduce the thickness and overall collapsed profile of the device.

Figure 14A:
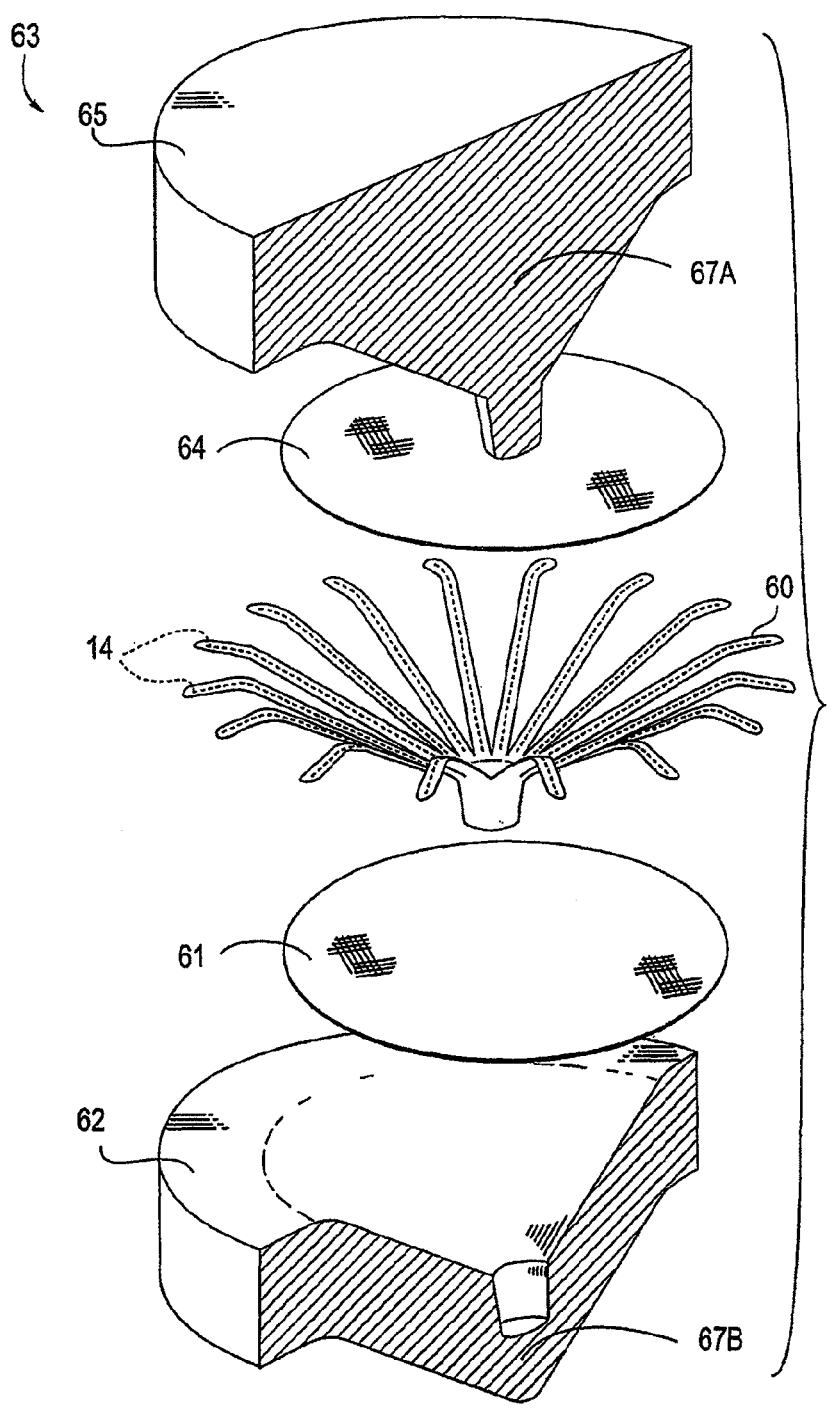
FIGS. 14A-14D include views of a bilaminar assembly for the making of an intracorporeal partitioning device, as well as views of the assembled device.
Figure 14B:
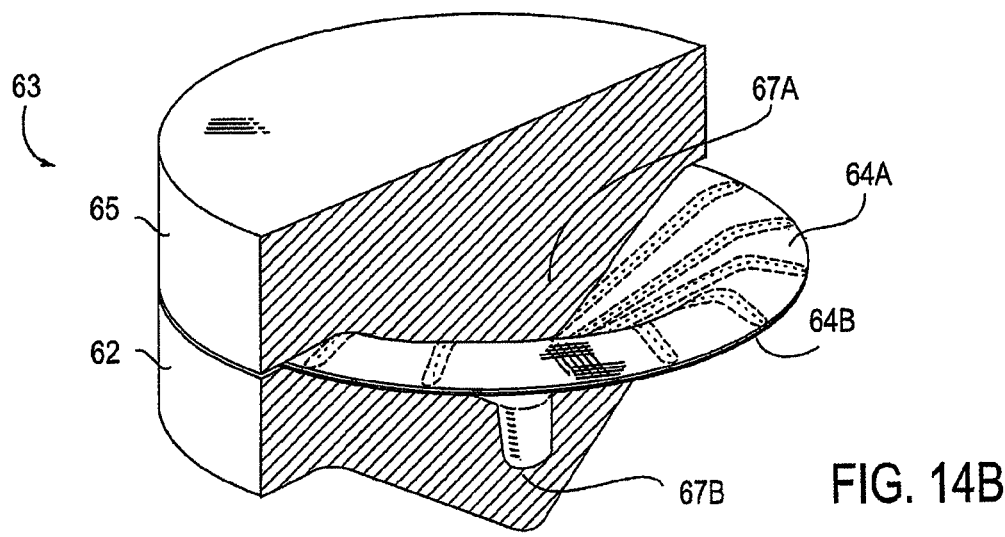
Figure 14C:
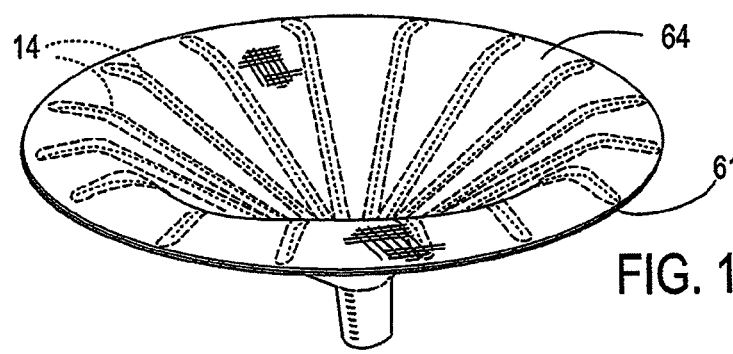
Figure 14D:
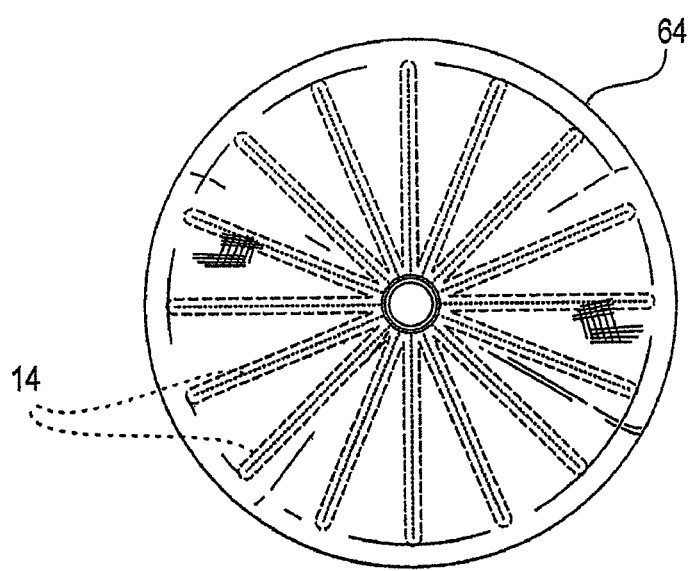

FIGS. 14A-14D include further views of a bilaminar assembly for the making of an intracorporeal partitioning device (as also depicted variously in preceding FIGS. 11-13) and views of the assembled device. FIG. 14A shows a perspective view of an exemplary device; FIG. 14B shows an exploded and partially cutaway view of the components of the device assembled for lamination; FIG. 14C provides of cutaway view of the device within the press in a closed position; and FIG. 14D provides a frontal view of the device after assembly.

In FIG. 14A, the upper or male platen 65 of a press 63 and the lower or female platen 62 are seen above and below, respectively, an awaiting assembly that includes, from top to bottom, a sheet of ePTFE 64, an assembly of polyethylene 60 covered ribs 14 that are formed into a cone-shaped configuration, and a bottom sheet of ePTFE 61. Around the periphery of the upper platen 65 is a rim portion 66A, and around the periphery of the lower platen 62 is a rim portion 66B. These two rim portions (66A and 66B) form complementary planar surfaces which serve to hold edges of the sheets of ePTFE fabric as the central portion is being subjected to being pressed by the complementary surfaces of the central portion or shaping portion 67A of the upper platen 65, and the central portion 67B of the lower platen 62. The closure of the two halves of the platen is depicted in the cutaway view of FIG. 14B. A perspective view of the device as it would emerge post-formation is seen in FIG. 14C; where the polyethylene encased ribs 14 may be seen. A frontal plane-flattening view of the device upon removal from the press is shown in FIG. 14D, again showing the polyethylene encased ribs 60A, the polyethylene now reformed from its native circular configuration. Details of this structure in a before-pressing form 60 and after-pressing pressing form 60A are shown in FIGS. 16, 17, and 21.

Figure 15A:
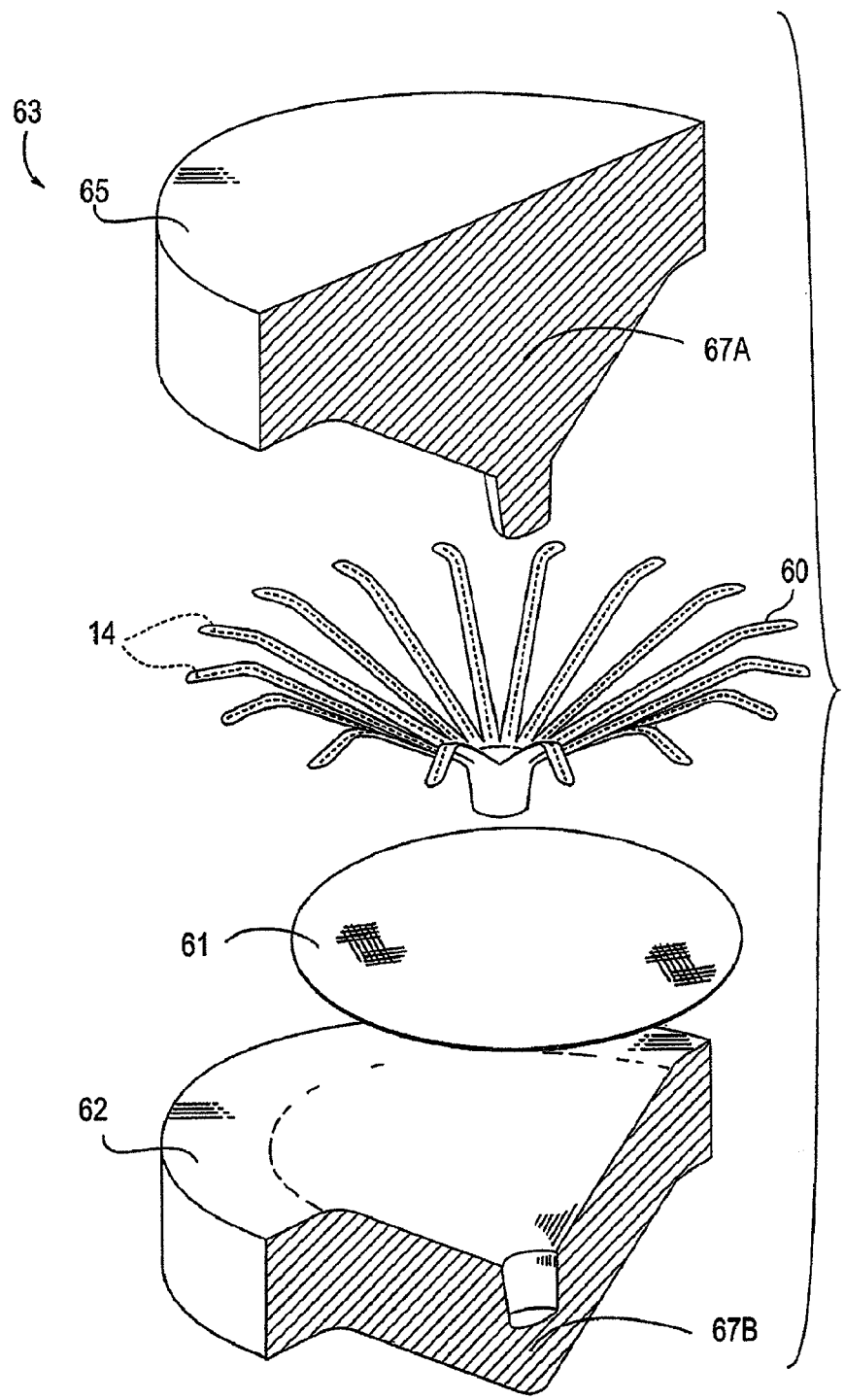
FIGS. 15A-15D include views of a unilaminar assembly for the making of an intracorporeal partitioning device, as well as views of the assembled device.
Figure 15B:
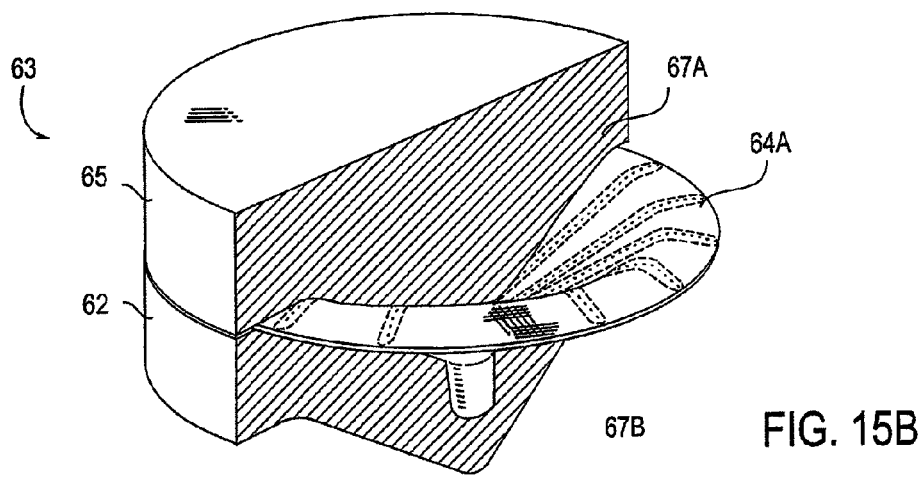
Figure 15C:
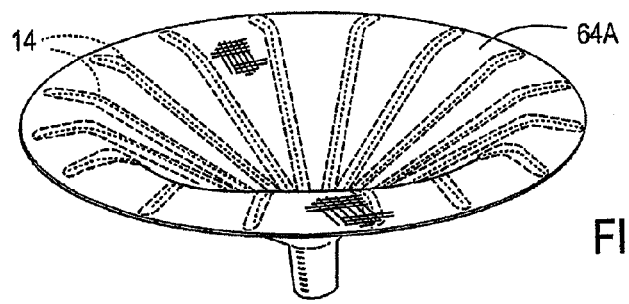
Figure 15D:
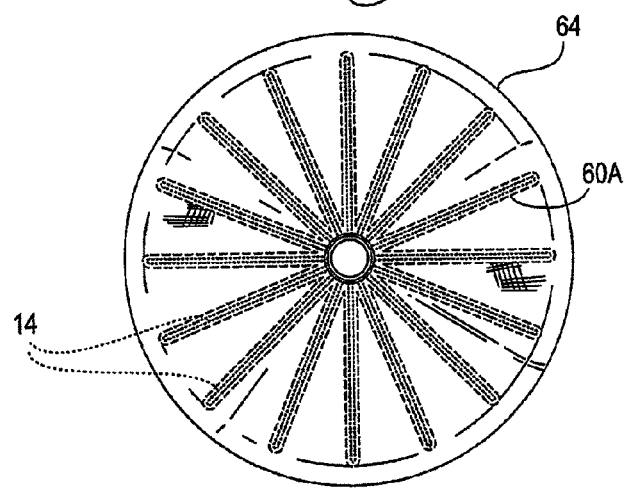

FIGS. 15A-15D include various views of a unilaminar assembly for the making of an intracorporeal partitioning device, as well as views of the assembled device. FIG. 15A shows an exploded and partially cutaway view of the components of the device assembled for lamination; FIG. 15B provides of cutaway view of the device within a press, the press in a closed position; FIG. 15C shows a perspective view of an exemplary device; FIG. 15D provides a frontal view of the device after assembly.

In FIG. 15A, the upper or male platen 65 of a press 63 and the lower or female platen 62 are seen above and below, respectively, an awaiting assembly that includes, from top to bottom, an assembly of polyethylene 60 covered ribs 14 that are formed into a cone-shaped configuration, and a bottom sheet of ePTFE 61 that will ultimately form a unilaminar device. Around the periphery of the upper platen 65 is a rim portion 66A, and around the periphery of the lower platen 62 is a rim portion 66B. These two rim portions (66A and 66B) form complementary planar surfaces which serve to hold edges of the sheets of ePTFE fabric as the central portion is being subjected to being pressed by the complementary surfaces of the central portion or shaping portion 67A of the upper platen 65, and the central portion 67B of the lower platen 62. The closure of the two halves of the platen is depicted in the cutaway view of FIG. 15B. A perspective view of the device as it would emerge post-formation is seen in FIG. 15C; where the polyethylene encased ribs 14 may be seen. A frontal plane-flattening view of the device upon removal from the press is shown in FIG. 15D, again showing the polyethylene encased ribs 60A, the polyethylene now reformed from its native circular configuration. Details of this structure in a before-pressing form 60 and after-pressing pressing form 60A are shown in FIGS. 16, 17, and 21.

An aspect of ePTFE material that relates to the internodal distances within the fabric is that such distance is preferably sufficient to accommodate the flow of melted polyethylene from the thermoplastic tubes 60 during the heating and pressuring period of embodiments of the forming process. As melted polyethylene intercalates into the ePTFE fabric and then solidifies in a reformed configuration on cooling, intermingled and interlocking zones of material continuity having been created between polyethylene and polytetra-fluoroethylene (PTFE). These fusion zones of interlocking zones of material continuity provide a firm bonding matrix that (1) secures the still-polyethylene-encased rib 14 to the adjacent one ePTFE sheet (in a unilaminar embodiment) or two ePTFE sheets (in a bilaminar embodiment, and thereby within the bilaminar structure formed by the two sheets) and (2), in a bilaminar embodiment, the adheres the two ePTFE sheets together to form a bilaminar structure.

Figure 16A:
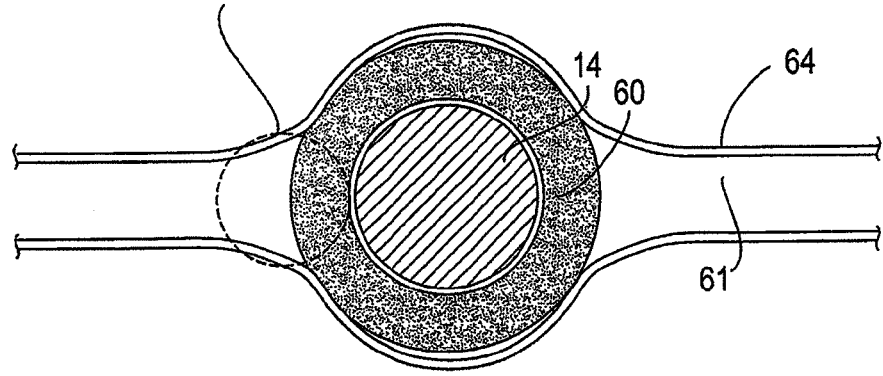
FIG. 16A shows a polyethylene-encased rib sandwiched between two sheets of ePTFE material as assembled prior to processing in a mold or press. In this embodiment, the rib is substantially cylindrical in form, or substantially circular in cross section.
Figure 16B:
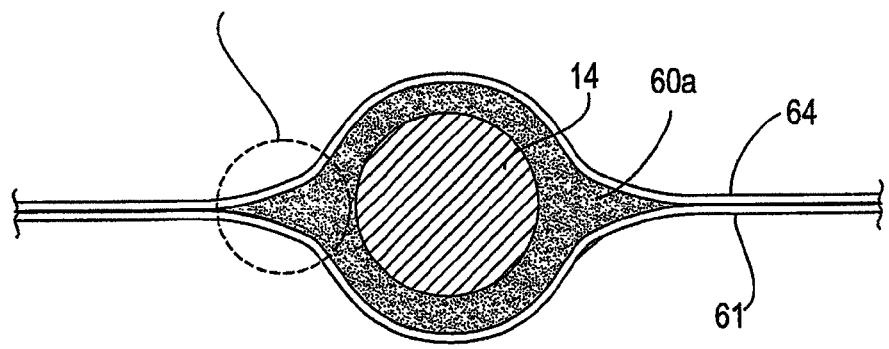
FIG. 16B shows the same materials after the application of heat and pressure, to form a bilaminar sheet, the sheets held together by melted and reformed polyethylene material to which they are both fused, a rib disposed within and adherent to the polyethylene.
Figure 17A:
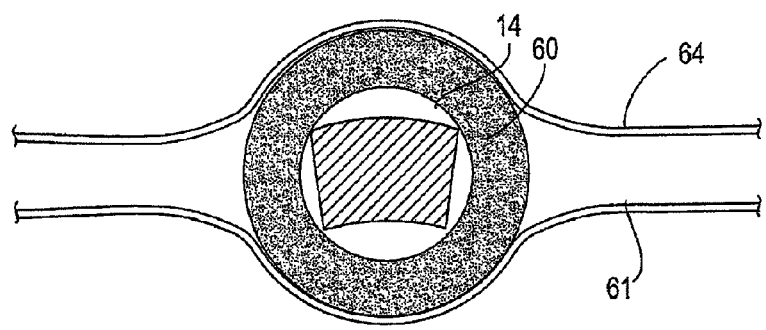
FIG. 17A shows a polyethylene-encased rib sandwiched between two sheets of ePTFE material as assembled prior to processing in a mold or press. In this embodiment, the rib is substantially rectangular, but curved in cross section.
Figure 17B:
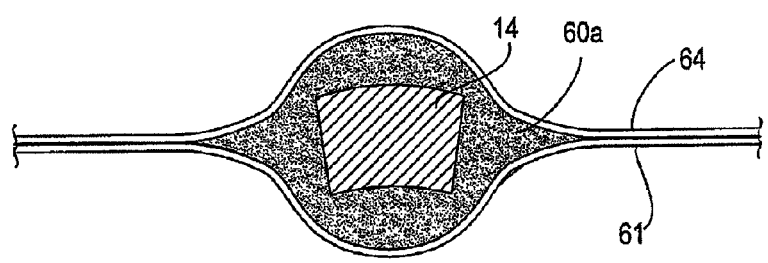
FIG. 17B shows the same materials after the application of heat and pressure, to form a bilaminar sheet, the sheets held together by melted and reformed polyethylene material to which they are both fused, a rib disposed within and adherent to the polyethylene.

FIGS. 16 and 17 provide views of two embodiments of a metallic rib encased in a polyethylene tube 60, prior to (A) and subsequent to (B) being fused within two ePTFE sheets (61 and 64), to form a bilaminar dPTFE sheet, the two sheets adhering to each other in the locale of the zone of fusion between the polyethylene and the ePTFE materials. FIGS. 16A and 16B depict a rib that is substantially circular in cross section. Similar embodiments (not shown) include those with cross sectional profiles that are somewhat flattened or elliptical. The cross sectional profile of ribs may vary, and various embodiments may provide advantages with regard, for example, to stiffness or to practical aspects of the assembly of the device. Other embodiments of ribs are more rectangular in cross section. FIGS. 17A and 17B depict a rib that is generally rectangular in cross section, though curved or arched as a whole in cross section in this particular embodiment, with a convex upper-facing surface and a concave lower-facing surface.

FIG. 16A provides a cross sectional view of a metallic rib 14, substantially circular in cross section, encased in a polyethylene tube 60, the tube disposed between the two ePTFE sheets 61 and 64 prior to application of pressure and heat. FIG. 16B provides a view of the same materials after heat and pressure to form a bilaminar device. The thermoplastic material that originally comprised tube 60 disposed over the rib 14, has reformed as polyethylene material 60A, which is fused into the porous matrix of the ePTFE sheets 61 and 64. (The polyethylene material represented by 60 in its native form and by 60A in its post-melt and reformed form is substantially conserved in terms of total volume, but it is redistributed as schematically depicted in FIGS. 16A-16B, as well as in FIGS. 17-21. In addition to the schematically depicted polyethylene 60 and 60A, also depicted schematically and not necessarily to scale are the relative sizes of the ribs 14 and the PTFE fabric 64.) The first and second ePTFE sheets thereby form a bilaminar ePTFE sheet, and at sites where the bilaminar sheet surrounds the thermoplastic material; the bilaminar ePTFE and the thermoplastic material solidify, thereby securing the sheets 61 and 64 to the ribs 14 and preventing their delamination during use of the partitioning device. The encircled detail within FIG. 16A that is labeled 21A is a reference to FIG. 21A which provides a more detailed of the ePTFE and polyethelene materials prior to their fusion during the lamination process, as described below. The encircled detail within FIG. 16B that is labeled 21B is a reference to FIG. 21B which provides a more detailed of the ePTFE and polyethelene materials after their fusion during the lamination process, as described below.

FIGS. 17A and 17B provide a representation of an embodiment of the device wherein the rib 14 is substantially rectangular in cross section, but wherein the process of forming a device is otherwise substantially parallel to the sequence shown in FIGS. 16A and 16B. FIG. 17A provides a cross sectional view of a metallic rib 14, substantially rectangular in cross section, encased in a polyethylene tube 60, the tube disposed between the two ePTFE sheets 61 and 64 prior to application of pressure and heat to form a bilaminar device. FIG. 17B provides a view of the same materials after heat and pressure. The thermoplastic material that originally comprised tube 60 disposed over the rib 14 has reformed as polyethylene material 60A, which is fused into the porous matrix of the ePTFE sheets 61 and 64. The first and second ePTFE sheets thereby form a bilaminar ePTFE sheet, and at sites where the bilaminar sheet surrounds the thermoplastic material; the bilaminar ePTFE and the thermoplastic material solidify, thereby securing the sheets 61 and 64 to the ribs 14 and preventing their delamination during use of the partitioning device. Sheets may be formed of either porous or non-porous ePTFE, as well as other suitable biocompatible materials, as described further below.

In embodiments where only a single sheet of ePTFE is used, a unilaminar structure is formed, with the ribs 14 adhering to the ePTFE sheet 61 by way of the melted and reformed polyethylene that originally comprised the thermoelastic tube 60 surrounding rib 14. These unilaminar embodiments are described further below, and depicted in FIGS. 18 and 19. In both cases, i.e., the unilaminar and bilaminar embodiments, the reforming of the polyethylene which originally encases the rib 14 to a configuration that intercalates through the ePTFE weave, it is the reformation of the polyethylene that is substantially responsible for the integration of the ePTFE and the polyethylene-encased ribs(s) into an integrated structure.

Figure 18A:
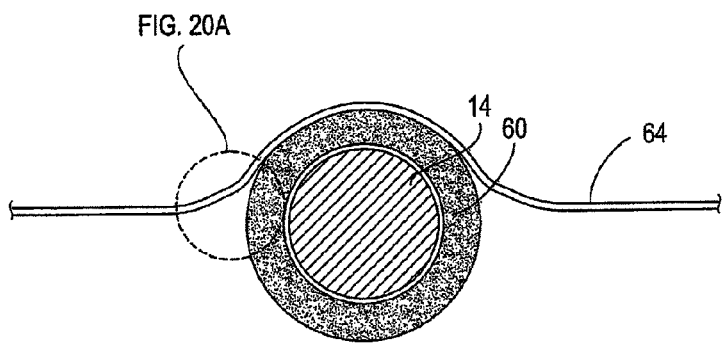
FIG. 18A shows a polyethylene-encased rib overlaying a sheet of ePTFE material as assembled prior to processing in a mold or press. In this embodiment, the rib is substantially circular in cross section.
Figure 18B:
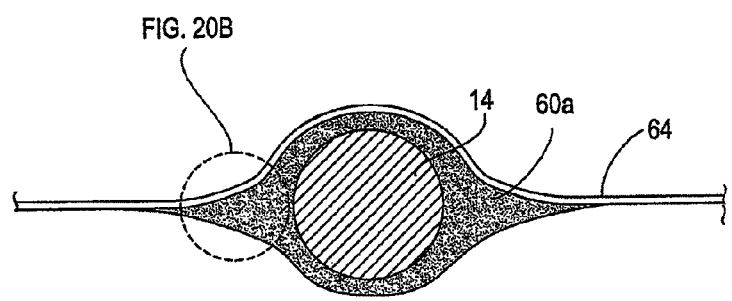
FIG. 18B shows the same materials after the application of heat and pressure, to form a unilaminar sheet fused to a rib by the melted and reformed polyethylene, the polyethylene interposed between the rib and the ePTFE sheet, adhering to both.

In embodiments where only a single sheet of ePTFE is used, a unilaminar structure is formed, with the ribs 14 adhering to the single ePTFE sheet 61 by way of the melted and reformed polyethylene that originally comprised the thermoelastic tube 60 surrounding rib 14, the polyethylene material still encasing the rib. Unilaminar embodiments of the invention are depicted in FIGS. 18 and 19. FIG. 18A shows a cross sectional view of a rib, substantially circular in cross section, encased in a polyethylene tube 60, the tube disposed adjacent to ePTFE sheets 61 prior to application of pressure and heat. FIG. 18B provides a view of the same materials after application of heat and pressure. The thermoplastic material that originally comprised tube 60 disposed over the rib 14 has fused into the porous matrix of the ePTFE sheet 61.

The encircled detail within FIG. 18A that is labeled 20A is a reference to FIG. 20A which provides a more detailed of the ePTFE and polyethelene materials prior to their fusion during the lamination process, as described below. The encircled detail within FIG. 18B that is labeled 20B is a reference to FIG. 20B which provides a more detailed view of the ePTFE and polyethelene materials after their fusion during the lamination process, as described below.

Figure 19A:
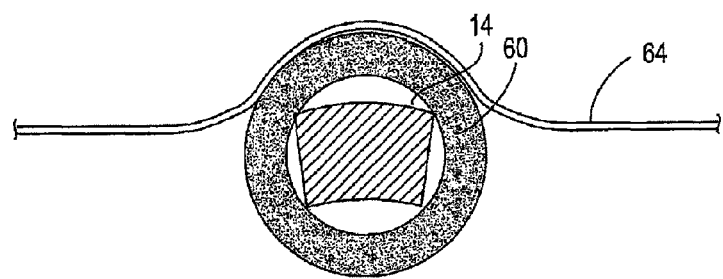
FIG. 19A shows a polyethylene-encased rib overlaying a sheet of ePTFE material as assembled prior to processing in a mold or press. In this embodiment, the rib is substantially rectangular but curved in cross section.
Figure 19B:
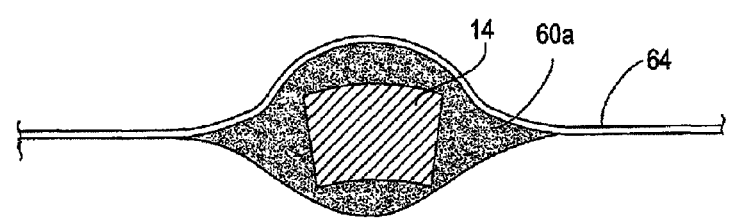
FIG. 19B shows the same materials after the application of heat and pressure, to form a unilaminar sheet fused to a rib by the melted and reformed polyethylene, the polyethylene interposed between the rib and the ePTFE sheet, adhering to both.

Similarly, FIGS. 19A shows a cross sectional view of a rib, generally rectangular in cross section, encased in a polyethylene tube 60, the tube adjacent to ePTFE sheet 61 prior to application of pressure and heat. FIG. 19B provides a view of the same materials after heat and pressure. The thermoplastic material that originally comprised tube 60 disposed over the rib 14 has fused into the porous matrix of the ePTFE sheet 61.

In some embodiments of the method, a cooling step is applied following the application of pressure and heat. A relatively passive cooling method is appropriate for some embodiments, and can be achieved by simply placing the mold on a cold surface (for example, a chilled block of copper) or by submerging it in any suitable cold medium such as chilled water. In other embodiments, more active, permeative, or quick cooling is preferred, and may be accomplished by circulating any suitable coolant (for example, chilled water, liquid nitrogen) through cooling channels built into the lamination mold body to bring the temperature into a range of about 0.degree. F. to about 32.degree. F.

While porous ePTFE material is included in typical embodiments, non-porous ePTFE may be appropriate for some embodiments. The choice of using non-porous or porous ePTFE depends on the intended use or desired features when the partitioning device is placed in the heart. A porous membrane can advantageously function as a filter-like barrier that allows blood through-flow, but blocks transit of particles or emboli. On the other hand, in some medical applications it may be desirable to form a significant seal between two cardiac compartments with the intervention of the partitioning device, in which case a non-porous ePTFE may be preferred.

Further, the membrane 11 may also be formed of other suitable biocompatible polymeric materials such as, by way of example, may include Nylon, PET (polyethylene terephthalate), and polyesters such as Hytrel. The membrane 11 may advantageously be foraminous in nature to facilitate tissue ingrowth after deployment within the patient's heart, and further, to provide an advantageous matrix for bonding with melted polyethylene material, as for example, from a thermoplastic tube 60. The delivery catheter 32 and the guiding catheter 31 may be formed of suitable high strength polymeric material such as, by way of example, polyetheretherketone (PEEK), polycarbonate, PET, and/or Nylon. Braided composite shafts may also be employed.

FIGS. 20 and 21 provide schematic views of the lamination zones of the device, at microscopic scale. Embodiments of the porous or foraminous ePTFE sheets may have internodal distances between woven fabric strands that range between about 5 and about 200 microns, as described above. The internodal areas delineated by the fibers also provide space into which polyethylene material from the thermoplastic tubes 60 intercalates as it melts and reforms during embodiments of the lamination process. As melted polyethylene material intercalates into the unmelted ePTFE material and then solidifies into a reformed configuration on cooling, intermingled and interlocking zones of respective material-material continuity are created between polyethylene and poly-tetra-fluoro-ethylene (PTFE). The continuity of the PTFE fibers remains substantially unchanged, even though the fibers may be stretched, and the polyethylene forms a continuous solid that includes the PTFE fibers within it. These interlocking zones of material continuity provide a firm bonding matrix that both (1) adheres the two sheets of the bilaminar structure together, and (2) secures the rib 14 to and within the bilaminar structure. The formation of integrated laminar structures that include one or two ePTFE sheets and thermoplastic material entrapping a rib is depicted in FIGS. 20 and 21; these are schematic views, drawn such that the internodal distances appear at a scale that is larger than that of the device as a whole.

Figure 20A:
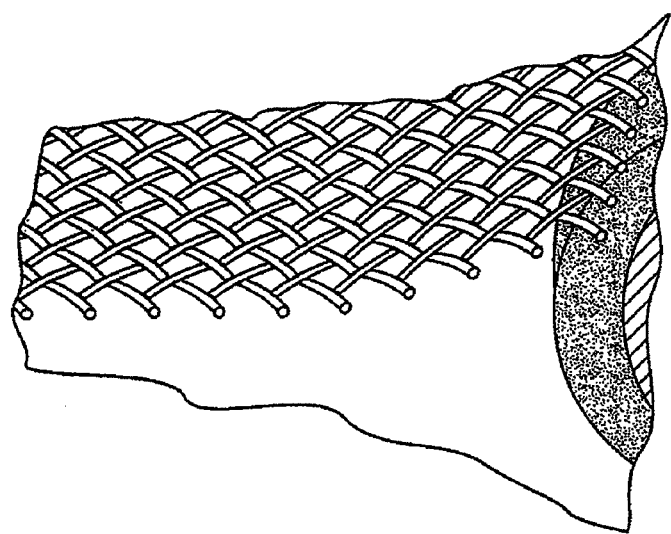
FIGS. 20A and 20B schematically depict the formation of a unilaminar integrated structure from the polyethylene-encased rib and ePTFE material by the melting and solidified reformed polythethylene to create interlocking continuities between the ePTFE and the polyethylene. This structure also depicts a portion of a larger bilaminar structure, such as a portion immediately overlaying a rib.
Figure 20B:
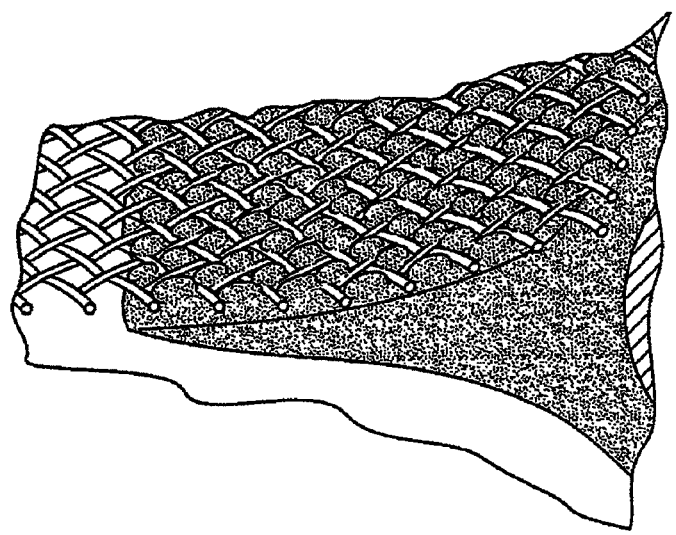

FIGS. 20A and 20B schematically depict the formation of a unilaminar integrated structure from the polyethylene-encased rib and ePTFE material by the melting and solidified reformed polythethylene to create interlocking continuities between the ePTFE and the polyethylene. This structure also depicts a unilaminar or split-laminar portion of a larger bilaminar structure, such as a portion immediately overlaying a rib 14. FIG. 20A depicts a woven sheet of ePTFE disposed over or adjacent to a portion of the wall of a polyethylene tube encasing a rib before being subjected to pressure and heat within a press. FIG. 20B depicts the unified structure after the application of heat and pressure, and after the polyethylene has melted and reformed within and around the weave of the ePTFE fabric.

Figure 21A:
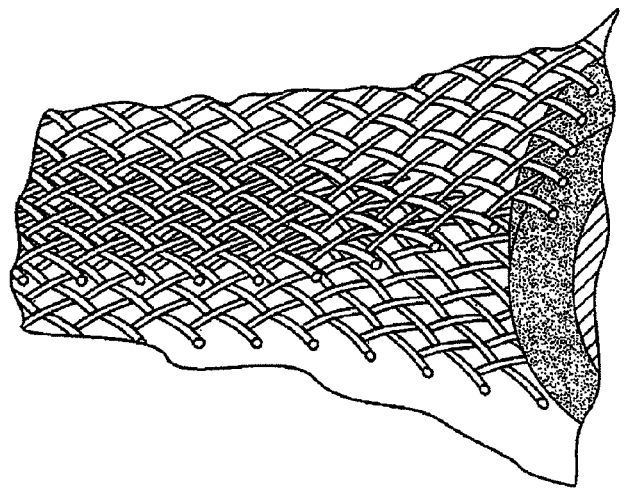
FIGS. 21A and 21B schematically depict the formation of a bilaminar integrated structure from the polyethylene-encased rib and ePTFE material by the melting and solidified reformed polythethylene to create interlocking continuities between the ePTFE and the polyethylene.
Figure 21B:
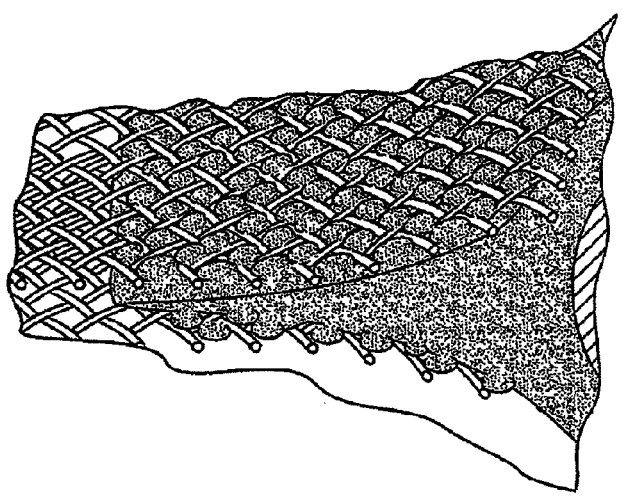

FIGS. 21A and 21B schematically depict the formation of a bilaminar integrated structure from the polyethylene-encased rib and ePTFE material by the melting and solidified reformed polythethylene to create interlocking continuities between the ePTFE and the polyethylene. FIG. 21A depicts two woven sheets of ePTFE disposed, respectively, over and under a portion of the wall of a polyethylene tube encasing a rib before being subjected to pressure and heat within a press.

FIG. 21B depicts the unified structure after the application of heat and pressure, and after the polyethylene has melted and reformed within and around the weave of the ePTFE fabric. This bilaminar structure occurs in areas not immediately overlaying a rib 14, but rather in the area that lies immediately adjacent to a rib 14, and spreading out peripherally, thereby creating a substantial area of mutual connection between the two ePTFE sheets.

Figure 22:
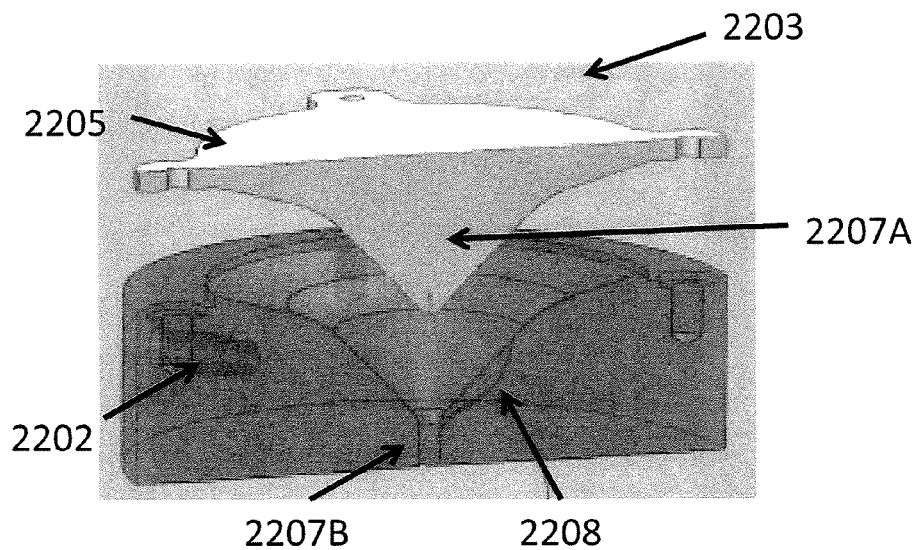

FIG. 22 shows an exploded and partially cutaway view of the components of the assembly for lamination. FIG. 22 illustrates an alternative embodiment of an assembly for the making of an intracorporeal partitioning device, wherein the device is laminated in a partially compressed, i.e. not-free state. This assembly may be configured to assemble either a unilaminar or bilaminar device. The assembly depicted in FIG. 22 is similar to the assemblies described above with references to FIGS. 14 and 15, however the assembly of FIG. 22 is configured to laminate the device in its non-free state.

Figure 23A:
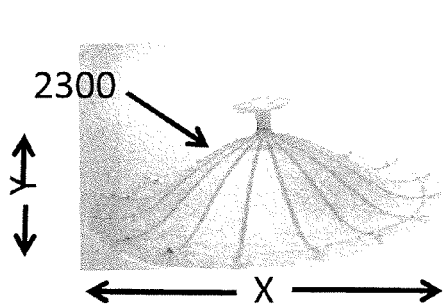

As described above in reference to FIGS. 14 and 15, the implants are assembled, or laminated, in their free, heat shaped configuration. A resulting device 2300 is shown in FIG. 23A, having a free diameter of X, for example. The devices described herein are generally configured for implantation into a ventricle of a patient's heart. In some embodiments, the patient's ventricle may be smaller in diameter than the free size of the device, or more specifically, smaller than the diameter X, as shown in FIG. 23A. In some specific cases, the diameter of the ventricle may be 20 to 30% smaller than the free diameter X of the device 2300. For example, in a healthy heart, the end-diastolic dimension of the left ventricle may range from 36-56 mm and the end-systolic dimension of the left ventricle may range from 20-40 mm (A left ventricle in heart failure would typically have larger dimensions). Therefore, once implanted, a device laminated in its free state would likely be held in a contracted position (i.e. a loaded configuration with a decreased diameter) and not return to a free state and its free, or unloaded, dimension (e.g. diameter). Therefore, the membrane material will likely bunch between the struts to accommodate the device moving into the contracted state upon implantation. Excess membrane material may lead to, at least, a more expensive device, a larger collapsed configuration (necessitating larger guide and delivery catheters), improper sealing or engagement with the ventricle wall, and/or a combination thereof. Therefore, it may be desirable, in some configurations to laminate the frame of the device in a pre-loaded, or non-free, state, thereby reducing the amount of membrane material utilized to laminate the device.

In FIG. 22, the upper or male platen 2205 of a press 2203 and the lower or female platen 2202 are seen above and below, respectively. As described above, around the periphery of the upper platen 2205 is a rim portion, and around the periphery of the lower platen 2202 is a rim portion. These two rim portions form complementary planar surfaces which serve to hold edges of the sheets of ePTFE fabric as the central portion is being subjected to being pressed by the complementary surfaces of the central portion or shaping portion 2207A of the upper platen 2205, and the central portion 2207B of the lower platen 2202. A perspective view of the device as it would emerge post-formation is seen in FIG. 23A. A comparison of the assembly in FIG. 22 and FIG. 14 or 15 will show that the shaping portions 2207A and B have a steeper angle than the shaping portions 67A and 67B in FIGS. 14 and 15. Furthermore, the height of the assembly (and the resulting device) is taller in the assembly of FIG. 22. The assembly of FIG. 22 thereby holds the device components (particularly the frame) in a pre-loaded configuration with a decreased diameter. Furthermore, as shown by line 2208, the curve of the shaping elements 2207A and 2207B may follow the curve the struts will undergo in their pre-loaded configuration. Alternatively, an assembly with a straight (not-curved 2208) shaping element may be utilized, however, in some instances; a straight shaping element may over constrain the struts in their pre-loaded configuration.

Figure 23B:
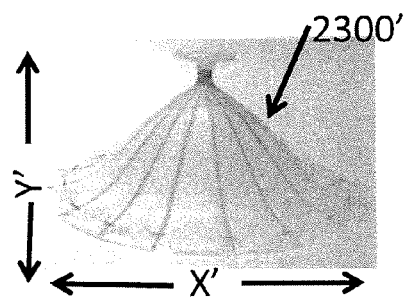

As shown in FIG. 23B, a device resulting from the assembly fixture shown in FIG. 22 has a diameter X' which is smaller than diameter X as shown in FIG. 23A, and a height Y' which is taller than Y as shown in FIG. 23A. In one specific example, an implant with diameter X equal to 85 mm might be compared to an implant with diameter X' equal to 75 mm. In some embodiments, it may be noted that devices assembled in a pre-loaded state, may have increased stability and/or a decreased propensity to inverting (flipping inside out) during delivery, implantation, and/or the life of the device.

Figure 24A:
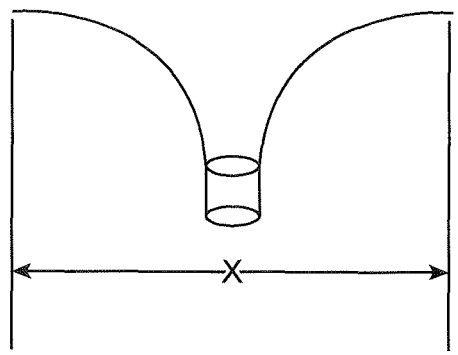
FIGS. 24A-24C illustrate a cross-section of a loaded frame in its free state (FIG. 24A), after lamination (FIG. 24B), and implanted (FIG. 24C).
Figure 24B:
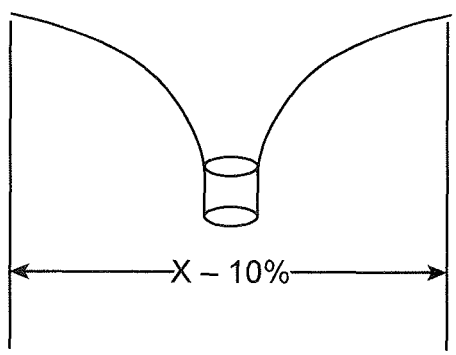
Figure 24C:
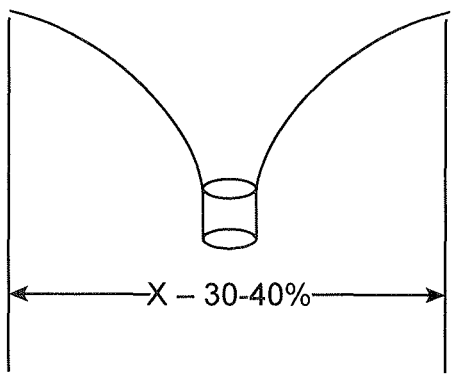

FIGS. 24A-24C illustrate a cross-section of a loaded frame in its free state or unstressed configuration (FIG. 24A), after lamination with an assembly fixture as shown in FIG. 22 (FIG. 24B), and implanted (FIG. 24C). The frame as shown in FIG. 24A may be compared to the device shown in FIGS. 9 and 10, which illustrate the reinforcing frame 13 in an unstressed configuration and include the ribs 14 and the hub 12. The ribs 14 have a length L of about 1 to about 8 cm, preferably, about 1.5 to about 4 cm for most left ventricle deployments. The proximal ends 16 have a flared construction. As shown in FIG. 24A, the frame in its free, pre-assembled state, may have a diameter of X (e.g. 80 mm). As shown in FIG. 24B, the frame in its pre-loaded, assembled state, may have a diameter of X-10% (e.g. 72 mm). For example, the frame may be pre-loaded by 10% in the assembly fixture. As shown in FIG. 24C, the frame in its loaded, implanted state, may have a diameter of X-30-40% (e.g. 56-64 mm). For example, the frame may be pre-loaded an additional 20-30% in the patient's ventricle, specifically during diastole. Although percentages of loading and/or pre-loading and diameter reduction are listed by way of providing exemplary loading configurations, such examples are for purposes of clarity of understanding only, and are not intended to be limiting. It should be understood that the frame may be loaded and/or pre-loaded and reduced in diameter to any suitable size and configuration.

Figure 25A:
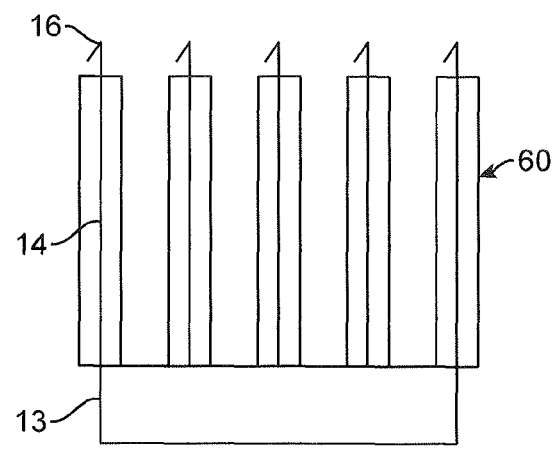
FIGS. 25A-25C illustrate a first, second, and third embodiment showing the frame of the device described herein having sleeves. As shown, the device may include full sleeves disposed along the full length of the struts (FIG. 25A), partial sleeves staggered along the length of the struts (FIG. 25B), or shortened sleeves (FIG. 25C).
Figure 25B:
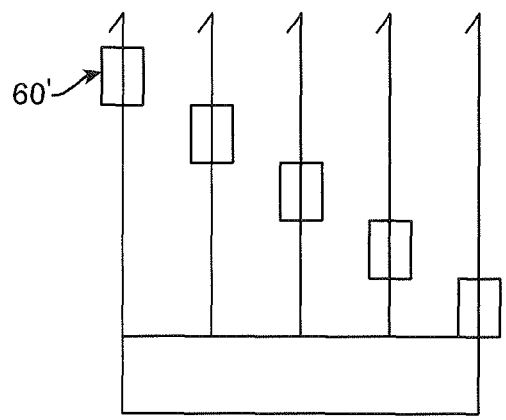
Figure 25C:
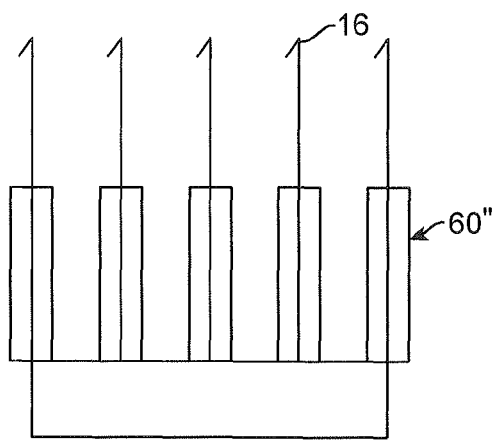

As described above, embodiments of the partitioning device 10, both unilaminar and bilaminar embodiments, are conveniently formed by placing a thermoplastic tube 60, e.g. polyethylene or high density polyethylene (HDPE), over the ribs 14 of the frame 13 as shown in FIG. 25A until the proximal ends 16 of the ribs 14 extend out the ends of the thermoplastic tubes to form thermoplastic-encased ribs. FIGS. 25A-25C illustrate a first, second, and third embodiment showing the frame of the device described herein having sleeves, or more specifically thermoplastic tubes 60. As shown, the device may include full sleeves 60 disposed along the full length of the struts (FIG. 25A), partial sleeves 60' staggered along the length of the struts (FIG. 25B), or shortened sleeves 60" (FIG. 25C). As shown in FIG. 25B, by reducing the amount of tubing used, and by staggering the positioning of the tubing along the length of the struts 14, the implants collapsed profile may be reduced. As shown in FIG. 25C, a reduction in profile could also be accomplished by shortening the length of the tubes, keeping them away from the perimeter of the device, or proximal ends 16 of the ribs 14, where most of the profile size is accumulated. In an alternative embodiment, a frame may be disposed between two sheets, and the sheets may be fused together to form the assembled implant without the need for sleeves, or more specifically thermoplastic tubes. For example, a method of securing a polymeric sheet to rib components of a frame structure may include the steps of providing an assembly, the assembly comprising a frame structure disposed between a first and second polymeric sheet; and heating the assembly under pressure to fuse the first polymeric sheet to the second polymeric sheet around the frame structure to form a fused sheet. In some embodiments, the polymeric sheets of material may be ePTFE.

Unless defined otherwise, all technical terms used herein have the same meanings as commonly understood by one of ordinary skill in the art of interventional cardiology. Specific methods, devices, and materials are described in this application, but any methods and materials similar or equivalent to those described herein can be used in the practice of the present invention. While embodiments of the invention have been described in some detail and by way of exemplary illustrations, such illustration is for purposes of clarity of understanding only, and is not intended to be limiting. Various terms have been used in the description to convey an understanding of the invention; it will be understood that the meaning of these various terms extends to common linguistic or grammatical variations or forms thereof. It will also be understood that when terminology referring to devices or equipment has used trade names, brand names, or common names, that these names are provided as contemporary examples, and the invention is not limited by such literal scope. Terminology that is introduced at a later date that may be reasonably understood as a derivative of a contemporary term or designating of a subset of objects embraced by a contemporary term will be understood as having been described by the now contemporary terminology. Further, any one or more features of any embodiment of the invention can be combined with any one or more other features of any other embodiment of the invention, without departing from the scope of the invention. Still further, it should be understood that the invention is not limited to the embodiments that have been set forth for purposes of exemplification, but is to be defined only by a fair reading of claims that are appended to the patent application, including the full range of equivalency to which each element thereof is entitled.

Terms such a "element", "member", "device", "section", "portion", "step", "means" and words of similar import, when used herein shall not be construed as invoking the provisions of 35 U.S.C. .sctn.112(6) unless the following claims expressly use the terms "means" followed by a particular function without specific structure or "step" followed by a particular function without specific action. All patents and patent applications referred to above are hereby incorporated by reference in their entirety.

What is claimed is:

1. A method of securing a polymeric sheet to rib components of a frame structure, wherein the rib components are jointed at a hub to form an expandable and collapsible implant, comprising:
   disposing a tube comprising thermoplastic material over each of one or more rib components of the frame;
   forming an assembly by applying the thermoplastic-encased rib adjacent to at least one polymeric sheet of material; and
   heating the assembly to fuse the sheet to the thermoplastic material to form a fused sheet, the fusion occurring by the heating and reforming of the thermoplastic material to the sheet, the rib remaining within the reformed thermoplastic material, wherein the implant is adapted to span a left ventricle.

2. The method of claim 1, further comprising the step of applying pressure to the assembly to form a fused sheet.

3. The method of claim 1, wherein the disposing step further comprises forming a thermoplastic-material-encased rib.

4. The method of claim 1, wherein the disposing step further comprises forming thermoplastic-material-encased ribs having proximal portions that are not encased in the thermoplastic material.

5. The method of claim 1, wherein the disposing step further comprises forming thermoplastic-material-encased ribs having tissue-penetrating proximal ends that are not encased in the thermoplastic material.

6. The method of claim 1, wherein the disposing step further comprises forming thermoplastic-material-encased ribs, wherein the thermoplastic material is disposed over a first portion of a first rib and a second portion of a second rib, wherein the first and second ribs are adjacent to one another and the first portion is at a different position along the length of the rib than the second portion.

7. The method of claim 1, wherein the at least one polymeric sheet of material comprises ePTFE.

8. The method of claim 1, wherein the fused sheet is a unilaminar sheet.

* * * * *